United States Patent
Miao et al.

(10) Patent No.: US 12,325,759 B2
(45) Date of Patent: *Jun. 10, 2025

(54) ANTI-VEGF-ANTI-PD-L1 BISPECIFIC ANTIBODY, PHARMACEUTICAL COMPOSITION OF SAME, AND USES THEREOF

(71) Applicant: BIOTHEUS INC., Guangdong (CN)

(72) Inventors: Xiaoniu Miao, Guangdong (CN); Cheng Chen, Guangdong (CN); Zhijun Yuan, Guangdong (CN); Weifeng Huang, Guangdong (CN); Andy Tsun, Guangdong (CN); Joanne Tsoyue Sun, Guangdong (CN)

(73) Assignee: BIOTHEUS INC., Guangdong (CN)

( * ) Notice: Subject to any disclaimer, the term of this patent is extended or adjusted under 35 U.S.C. 154(b) by 214 days.

This patent is subject to a terminal disclaimer.

(21) Appl. No.: 18/023,701

(22) PCT Filed: Aug. 30, 2021

(86) PCT No.: PCT/CN2021/115308
§ 371 (c)(1),
(2) Date: Feb. 27, 2023

(87) PCT Pub. No.: WO2022/042719
PCT Pub. Date: Mar. 3, 2022

(65) Prior Publication Data
US 2023/0340158 A1  Oct. 26, 2023

(30) Foreign Application Priority Data
Aug. 31, 2020  (CN) .......................... 202010897917.1

(51) Int. Cl.
C07K 16/46 (2006.01)
A61P 35/00 (2006.01)

(52) U.S. Cl.
CPC ............ *C07K 16/468* (2013.01); *A61P 35/00* (2018.01); *C07K 2317/565* (2013.01)

(58) Field of Classification Search
None
See application file for complete search history.

(56) References Cited

U.S. PATENT DOCUMENTS

| | | |
|---|---|---|
| 2013/0034559 A1 | 2/2013 | Queva et al. |
| 2018/0030137 A1 | 2/2018 | Van Eenennaam et al. |
| 2018/0291103 A1 | 10/2018 | Xu et al. |
| 2019/0177416 A1 | 6/2019 | Ting et al. |
| 2020/0172623 A1 | 6/2020 | Tian et al. |
| 2021/0340239 A1 | 11/2021 | Li et al. |
| 2022/0002418 A1 | 1/2022 | Zhu et al. |
| 2022/0041702 A1 | 2/2022 | Liu et al. |
| 2022/0315658 A1 | 10/2022 | Xu et al. |
| 2023/0031229 A1 | 2/2023 | Beirnaert |
| 2023/0399391 A1 | 12/2023 | Bachner et al. |

FOREIGN PATENT DOCUMENTS

| | | | |
|---|---|---|---|
| CN | 102753577 A | 10/2012 | |
| CN | 103254309 | 8/2013 | |
| CN | 103965363 A | 8/2014 | |
| CN | 107849130 A | 3/2018 | |
| CN | 109053895 A | 12/2018 | |
| CN | 109096396 A | 12/2018 | |
| CN | 109942712 A | 6/2019 | |
| CN | 110003333 A | 7/2019 | |
| CN | 110305210 A | 10/2019 | |
| CN | 110563849 A | 12/2019 | |
| CN | 110627906 A | 12/2019 | |
| CN | 110835375 A | 2/2020 | |
| CN | 112480253 A | 3/2021 | |
| EP | 3348571 A1 | 7/2018 | |
| WO | WO-9845331 A2 * | 10/1998 | ........... C07K 16/005 |
| WO | 03/016466 A2 | 2/2003 | |
| WO | 2015118175 A2 | 8/2015 | |

(Continued)

OTHER PUBLICATIONS

International Search Report and Written Opinion mailed Dec. 2, 2021, directed to International Application No. PCT/CN2021/115308; 18 pages.
"AOZ48530.1", GenBank (Nov. 1, 2016); 2 pages.
Dougan, M. et al., (Apr. 2018). "Targeting Cytokine Therapy to the Pancreatic Tumor Microenvironment Using PDL1-Specific VHHs," Cancer Immunology Research, vol. 6, No. 4; pp. 389-401.
Fang, T. et al., (Apr. 2019). "Remodeling of the Tumor Microenvironment by a Chemokine/Anti-PD-L1 Nanobody Fusion Protein," Molecular Pharmaceutics, vol. 16, No. 6; pp. 2838-2844.
Feng P. et al., (2017). "Preparation and application of anti-human PD-L1 monoclonal antibodies," pp. 879-883. English Abstract.

(Continued)

*Primary Examiner* — Daniel E Kolker
*Assistant Examiner* — James Ryland Melchior
(74) *Attorney, Agent, or Firm* — Neal, Gerber & Eisenberg LLP

(57) ABSTRACT

The present invention relates to the field of biomedicine and specifically relates to an anti-VEGF-anti-PD-L1 bispecific antibody, a pharmaceutical composition of same, and uses thereof. Specifically, the present invention relates to the bispecific antibody, which comprises: a VEGF-targeted first protein functional area and a PD-L1-targeted second protein functional area, wherein: the first protein functional area is an anti-VEGF antibody or an antigen-binding fragment thereof, or, the first protein functional area comprises a VEGF receptor or a fragment having a VEGF receptor function, and the second protein functional area is an anti-PD-L1 monoclonal antibody. The bispecific antibody of the present invention is capable of activating the immune system and blocking tumor angiogenesis at the same time, and provides great antitumor prospects.

34 Claims, 11 Drawing Sheets

Specification includes a Sequence Listing.

(56) References Cited

FOREIGN PATENT DOCUMENTS

| WO | 2017136562 A2 | 8/2017 | | |
|---|---|---|---|---|
| WO | 2019096121 A1 | 5/2019 | | |
| WO | 2019166622 A2 | 9/2019 | | |
| WO | 2019169212 A2 | 9/2019 | | |
| WO | 2019184909 A1 | 7/2020 | | |
| WO | 2020151761 A1 | 7/2020 | | |
| WO | WO-2021048725 A1 * | 3/2021 | ......... | A61K 47/6803 |

OTHER PUBLICATIONS

Guo, Y. et al., (Jun. 2022). "Phase I/IIa study of PM8001, a bifunctional fusion protein targeting PD-L1 and TGF-β, in patients with advanced tumors," retrieved from https://ascopubs.org/doi/pdf/10.1200/J CO.2022.40.16_suppl.2512.

Iezzi M. et al. (Feb. 19, 2018). "Single-Domain Antibodies and the Promise of Modular Targeting in Cancer Imaging and Treatment," Frontiers in Immunology, No. 9; 11 pages.

Knudson K.M. et al., (Feb. 2018). "M7824, a novel bifunctional anti-PD-L1/TGFβ Trap fusion protein, promotes anti-tumor efficacy as monotherapy and in combination with vaccine," Oncoimmunology, vo. 7, No. 5; pp. 1-14.

Lv, G. et al., (Jun. 28, 2019). "PET Imaging of Tumor PD-L1 Expression with a Highly Specific Nonblocking Single-Domain Antibody," Journal of Nuclear Medicine, vol. 61, No. 1; pp. 117-122.

Ravi, R. et al., (Feb. 2018). "Bifunctional immune checkpoint-targeted antibody-ligand traps that simultaneously disable TGFB enhance the efficacy of cancer immunotherapy," Nature Communications, vol. 9, No. 741; pp. 1-14.

Zhang, F. et al., (Mar. 7, 2017). "Structural basis of a novel PD-L1 nanobody for immune checkpoint blockade," Cell Discovery located at www.nature.com/celldisc; 12 pages.

Extended European Search Report for European Patent Application No. 21860551.7, dated Aug. 28, 2024.

First Office Action from Chinese Patent Application No. 202010897917.1 dated Apr. 20, 2024.

First Search Report from Chinese Patent Application No. 202010897917.1 dated Apr. 19, 2024.

Apte et al., (Mar. 7, 2019), "VEGF in Signaling and Disease: Beyond Discovery and Development," Cell 176, pp. 1248-1264.

* cited by examiner

SEQUENCE LISTING

```
<160> NUMBER OF SEQ ID NOS: 31

<210> SEQ ID NO 1
<211> LENGTH: 578
<212> TYPE: PRT
<213> ORGANISM: Artificial Sequence
<220> FEATURE:
<223> OTHER INFORMATION: ava-2GS-NSD HC

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
```

-continued

```
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
            165                 170                 175
Pro Ala Val Leu Gln Ser Ser Gly Leu Tyr Ser Leu Ser Ser Val Val
        180                 185                 190
Thr Val Pro Ser Ser Ser Leu Gly Thr Gln Thr Tyr Ile Cys Asn Val
    195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Ala
225                 230                 235                 240
Ala Gly Gly Pro Ser Val Phe Leu Phe Pro Pro Lys Pro Lys Asp Thr
            245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
        290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
            325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
            405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Gly Gly Gly Ser Gly Gly Gly Ser Gly Glu
    450                 455                 460
Val Gln Leu Gln Glu Ser Gly Gly Leu Val Gln Pro Gly Gly Ser
465                 470                 475                 480
Leu Arg Leu Ser Cys Ala Ala Ser Gly Phe Thr Phe Ser Ser Tyr Trp
            485                 490                 495
Met Tyr Trp Leu Arg Gln Ala Pro Gly Lys Gly Leu Glu Trp Val Ser
            500                 505                 510
Ser Ile Asn Ser Asp Ser Ser Ser Thr Tyr Tyr Arg Asp Ser Val Lys
        515                 520                 525
```

```
Gly Arg Phe Thr Ile Ser Arg Asp Asn Ala Lys Asn Thr Leu Tyr Leu
            530                 535                 540

Gln Met Asn Ser Leu Lys Ser Glu Asp Thr Ala Val Tyr Tyr Cys Ala
545                 550                 555                 560

Lys Asp Pro Gly Gly Tyr Ala Lys Gly Gln Gly Thr Gln Val Thr Val
                565                 570                 575

Ser Ser

<210> SEQ ID NO 2
<211> LENGTH: 588
<212> TYPE: PRT
<213> ORGANISM: Artificial Sequence
<220> FEATURE:
<223> OTHER INFORMATION: ava-4GS-NSD HC

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Gly Gly Gly Ser Gly Gly Gly Gly Ser Gly Gly
450                 455                 460

Gly Gly Ser Gly Gly Gly Ser Gly Glu Val Gln Leu Gln Glu Ser
465                 470                 475                 480

Gly Gly Gly Leu Val Gln Pro Gly Gly Ser Leu Arg Leu Ser Cys Ala
                485                 490                 495

Ala Ser Gly Phe Thr Phe Ser Ser Tyr Trp Met Tyr Trp Leu Arg Gln
            500                 505                 510

Ala Pro Gly Lys Gly Leu Glu Trp Val Ser Ser Ile Asn Ser Asp Ser
            515                 520                 525

Ser Ser Thr Tyr Tyr Arg Asp Ser Val Lys Gly Arg Phe Thr Ile Ser
530                 535                 540

Arg Asp Asn Ala Lys Asn Thr Leu Tyr Leu Gln Met Asn Ser Leu Lys
545                 550                 555                 560

Ser Glu Asp Thr Ala Val Tyr Tyr Cys Ala Lys Asp Pro Gly Gly Tyr
                565                 570                 575

Ala Lys Gly Gln Gly Thr Gln Val Thr Val Ser Ser
            580                 585

<210> SEQ ID NO 3
<211> LENGTH: 123
<212> TYPE: PRT
<213> ORGANISM: Artificial Sequence
<220> FEATURE:
<223> OTHER INFORMATION: Bevacizumab-VH

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

Ala Lys Tyr Pro His Tyr Gly Ser Ser His Trp Tyr Phe Asp Val
            100             105             110

Trp Gly Gln Gly Thr Leu Val Thr Val Ser Ser
        115                 120

<210> SEQ ID NO 4
<211> LENGTH: 329
<212> TYPE: PRT
<213> ORGANISM: Artificial Sequence
<220> FEATURE:
<223> OTHER INFORMATION: IgG1 CH(LALA)

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 5
<211> LENGTH: 115
<212> TYPE: PRT
<213> ORGANISM: Artificial Sequence
<220> FEATURE:
<223> OTHER INFORMATION: VHH-C-Ye-18-5

<400> SEQUENCE: 5

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Asn Ser Asp Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Pro Gly Gly Tyr Ala Lys Gly Gln Gly Thr Gln Val Thr
            100                 105                 110

Val Ser Ser
        115

<210> SEQ ID NO 6
<211> LENGTH: 11
<212> TYPE: PRT
<213> ORGANISM: Artificial Sequence
<220> FEATURE:
<223> OTHER INFORMATION: linker G4S2

<400> SEQUENCE: 6

Gly Gly Gly Gly Ser Gly Gly Gly Gly Ser Gly
1               5                   10

<210> SEQ ID NO 7
<211> LENGTH: 21
<212> TYPE: PRT
<213> ORGANISM: Artificial Sequence
<220> FEATURE:
<223> OTHER INFORMATION: linker G4S4

<400> SEQUENCE: 7

Gly Gly Gly Gly Ser Gly Gly Gly Gly Ser Gly Gly Gly Gly Ser Gly
1               5                   10                  15

Gly Gly Gly Ser Gly
            20

<210> SEQ ID NO 8
<211> LENGTH: 214
<212> TYPE: PRT
<213> ORGANISM: Artificial Sequence
<220> FEATURE:
<223> OTHER INFORMATION: ava-LC

<400> SEQUENCE: 8

Asp Ile Gln Met Thr Gln Ser Pro Ser Ser Leu Ser Ala Ser Val Gly
1               5                   10                  15

```
Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
         35                  40                  45

Tyr Phe Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 9
<211> LENGTH: 107
<212> TYPE: PRT
<213> ORGANISM: Artificial Sequence
<220> FEATURE:
<223> OTHER INFORMATION: Bevacizumab-VL

<400> SEQUENCE: 9

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
         35                  40                  45

Tyr Phe Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys
                100                 105
```

<210> SEQ ID NO 10
<211> LENGTH: 107
<212> TYPE: PRT
<213> ORGANISM: Artificial Sequence
<220> FEATURE:
<223> OTHER INFORMATION: human kappa light chain

<400> SEQUENCE: 10

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 11
<211> LENGTH: 578
<212> TYPE: PRT
<213> ORGANISM: Artificial Sequence
<220> FEATURE:
<223> OTHER INFORMATION: Luc-2GS-NSD HC

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Gly Gly Gly Ser Gly Gly Gly Gly Ser Gly Ser Glu
    450                 455                 460

Val Gln Leu Gln Glu Ser Gly Gly Gly Leu Val Gln Pro Gly Gly Ser
465                 470                 475                 480

Leu Arg Leu Ser Cys Ala Ala Ser Gly Phe Thr Phe Ser Ser Tyr Trp
                485                 490                 495

Met Tyr Trp Leu Arg Gln Ala Pro Gly Lys Gly Leu Glu Trp Val Ser
            500                 505                 510

Ser Ile Asn Ser Asp Ser Ser Ser Thr Tyr Tyr Arg Asp Ser Val Lys
        515                 520                 525

Gly Arg Phe Thr Ile Ser Arg Asp Asn Ala Lys Asn Thr Leu Tyr Leu
    530                 535                 540

Gln Met Asn Ser Leu Lys Ser Glu Asp Thr Ala Val Tyr Tyr Cys Ala
545                 550                 555                 560

Lys Asp Pro Gly Gly Tyr Ala Lys Gly Gln Gly Thr Gln Val Thr Val
                565                 570                 575

Ser Ser

<210> SEQ ID NO 12
<211> LENGTH: 588
<212> TYPE: PRT
<213> ORGANISM: Artificial Sequence
<220> FEATURE:
<223> OTHER INFORMATION: Luc-4GS-NSD HC

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30
```

-continued

```
Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Tyr Tyr Tyr Gly Thr Ser His Trp Tyr Phe Asp Val
             100                 105                 110

Trp Gly Gln Gly Thr Leu Val Thr Val Ser Ser Ala Ser Thr Lys Gly
         115                 120                 125

Pro Ser Val Phe Pro Leu Ala Pro Ser Ser Lys Ser Thr Ser Gly Gly
     130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Gln Thr Tyr Ile Cys Asn Val
         195                 200                 205

Asn His Lys Pro Ser Asn Thr Lys Val Asp Lys Lys Val Glu Pro Lys
     210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                 245                 250                 255

Leu Met Ile Ser Arg Thr Pro Glu Val Thr Cys Val Val Val Asp Val
             260                 265                 270

Ser His Glu Asp Pro Glu Val Lys Phe Asn Trp Tyr Val Asp Gly Val
         275                 280                 285

Glu Val His Asn Ala Lys Thr Lys Pro Arg Glu Glu Gln Tyr Asn Ser
     290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                 325                 330                 335

Pro Ile Glu Lys Thr Ile Ser Lys Ala Lys Gly Gln Pro Arg Glu Pro
             340                 345                 350

Gln Val Tyr Thr Leu Pro Pro Ser Arg Asp Glu Leu Thr Lys Asn Gln
         355                 360                 365

Val Ser Leu Thr Cys Leu Val Lys Gly Phe Tyr Pro Ser Asp Ile Ala
     370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                 405                 410                 415

Thr Val Asp Lys Ser Arg Trp Gln Gln Gly Asn Val Phe Ser Cys Ser
             420                 425                 430

Val Met His Glu Ala Leu His Asn His Tyr Thr Gln Lys Ser Leu Ser
         435                 440                 445

Leu Ser Pro Gly Gly Gly Gly Ser Gly Gly Gly Gly Ser Gly Gly
```

Gly Gly Ser Gly Gly Gly Ser Gly Glu Val Gln Leu Gln Glu Ser
465                 470                 475                 480

Gly Gly Gly Leu Val Gln Pro Gly Gly Ser Leu Arg Leu Ser Cys Ala
            485                 490                 495

Ala Ser Gly Phe Thr Phe Ser Ser Tyr Trp Met Tyr Trp Leu Arg Gln
            500                 505                 510

Ala Pro Gly Lys Gly Leu Glu Trp Val Ser Ser Ile Asn Ser Asp Ser
            515                 520                 525

Ser Ser Thr Tyr Tyr Arg Asp Ser Val Lys Gly Arg Phe Thr Ile Ser
            530                 535                 540

Arg Asp Asn Ala Lys Asn Thr Leu Tyr Leu Gln Met Asn Ser Leu Lys
545                 550                 555                 560

Ser Glu Asp Thr Ala Val Tyr Tyr Cys Ala Lys Asp Pro Gly Gly Tyr
            565                 570                 575

Ala Lys Gly Gln Gly Thr Gln Val Thr Val Ser Ser
            580                 585

<210> SEQ ID NO 13
<211> LENGTH: 123
<212> TYPE: PRT
<213> ORGANISM: Artificial Sequence
<220> FEATURE:
<223> OTHER INFORMATION: Luc VH

<400> SEQUENCE: 13

Glu Val Gln Leu Val Glu Ser Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 14
<211> LENGTH: 214
<212> TYPE: PRT
<213> ORGANISM: Artificial Sequence
<220> FEATURE:
<223> OTHER INFORMATION: Luc-LC

<400> SEQUENCE: 14

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

```
Tyr Phe Thr Ser Ser Leu His Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 15
<211> LENGTH: 107
<212> TYPE: PRT
<213> ORGANISM: Artificial Sequence
<220> FEATURE:
<223> OTHER INFORMATION: Luc VL

<400> SEQUENCE: 15

Asp Ile Gln Leu Thr Gln Ser Pro Ser Leu Ser Ala Ser Val Gly
 1               5                  10                  15

Asp Arg Val Thr Ile Thr Cys Ser Ala Ser Gln Asp Ile Ser Asn Tyr
                 20                  25                  30

Leu Asn Trp Tyr Gln Gln Lys Pro Gly Lys Ala Pro Lys Val Leu Ile
             35                  40                  45

Tyr Phe Thr Ser Ser Leu His Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys
            100                 105

<210> SEQ ID NO 16
<211> LENGTH: 567
<212> TYPE: PRT
<213> ORGANISM: Artificial Sequence
<220> FEATURE:
<223> OTHER INFORMATION: NSD-Elyea

<400> SEQUENCE: 16

Glu Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30
```

```
Trp Met Tyr Trp Leu Arg Gln Ala Pro Gly Lys Gly Leu Glu Trp Val
            35                  40                  45

Ser Ser Ile Asn Ser Asp Ser Ser Thr Tyr Tyr Arg Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
                 85                  90                  95

Ala Lys Asp Pro Gly Gly Tyr Ala Lys Gly Gln Gly Thr Gln Val Thr
                100                 105                 110

Val Ser Ser Asp Lys Thr His Thr Cys Pro Pro Cys Pro Ala Pro Glu
            115                 120                 125

Ala Ala Gly Gly Pro Ser Val Phe Leu Phe Pro Pro Lys Pro Lys Asp
        130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Asp Glu Leu Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Gly Gly Gly Ser Gly Gly Gly Gly Ser Gly
            340                 345                 350

Gly Gly Gly Ser Gly Gly Gly Gly Ser Gly Ser Asp Thr Gly Arg Pro
        355                 360                 365

Phe Val Glu Met Tyr Ser Glu Ile Pro Glu Ile Ile His Met Thr Glu
    370                 375                 380

Gly Arg Glu Leu Val Ile Pro Cys Arg Val Thr Ser Pro Asn Ile Thr
385                 390                 395                 400

Val Thr Leu Lys Lys Phe Pro Leu Asp Thr Leu Ile Pro Asp Gly Lys
                405                 410                 415

Arg Ile Ile Trp Asp Ser Arg Lys Gly Phe Ile Ile Ser Asn Ala Thr
            420                 425                 430

Tyr Lys Glu Ile Gly Leu Leu Thr Cys Glu Ala Thr Val Asn Gly His
        435                 440                 445
```

```
Leu Tyr Lys Thr Asn Tyr Leu Thr His Arg Gln Thr Asn Thr Ile Ile
            450                 455                 460

Asp Val Val Leu Ser Pro Ser His Gly Ile Glu Leu Ser Val Gly Glu
465                 470                 475                 480

Lys Leu Val Leu Asn Cys Thr Ala Arg Thr Glu Leu Asn Val Gly Ile
                485                 490                 495

Asp Phe Asn Trp Glu Tyr Pro Ser Ser Lys His Gln His Lys Lys Leu
                500                 505                 510

Val Asn Arg Asp Leu Lys Thr Gln Ser Gly Ser Glu Met Lys Lys Phe
            515                 520                 525

Leu Ser Thr Leu Thr Ile Asp Gly Val Thr Arg Ser Asp Gln Gly Leu
530                 535                 540

Tyr Thr Cys Ala Ala Ser Ser Gly Leu Met Thr Lys Lys Asn Ser Thr
545                 550                 555                 560

Phe Val Arg Val His Glu Lys
                565
```

```
<210> SEQ ID NO 17
<211> LENGTH: 205
<212> TYPE: PRT
<213> ORGANISM: Artificial Sequence
<220> FEATURE:
<223> OTHER INFORMATION: Elyea

<400> SEQUENCE: 17

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205
```

```
<210> SEQ ID NO 18
<211> LENGTH: 226
<212> TYPE: PRT
<213> ORGANISM: Artificial Sequence
<220> FEATURE:
```

<223> OTHER INFORMATION: Fc(LALA)

<400> SEQUENCE: 18

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 19
<211> LENGTH: 567
<212> TYPE: PRT
<213> ORGANISM: Artificial Sequence
<220> FEATURE:
<223> OTHER INFORMATION: Elyea-NSD

<400> SEQUENCE: 19

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110
```

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Ala Ala Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Gly
            420                 425                 430

Gly Gly Gly Ser Gly Gly Gly Gly Ser Gly Gly Gly Gly Ser Gly Gly
        435                 440                 445

Gly Gly Ser Gly Glu Val Gln Leu Gln Glu Ser Gly Gly Gly Leu Val
    450                 455                 460

Gln Pro Gly Gly Ser Leu Arg Leu Ser Cys Ala Ala Ser Gly Phe Thr
465                 470                 475                 480

Phe Ser Ser Tyr Trp Met Tyr Trp Leu Arg Gln Ala Pro Gly Lys Gly
                485                 490                 495

Leu Glu Trp Val Ser Ser Ile Asn Ser Asp Ser Ser Ser Thr Tyr Tyr
            500                 505                 510

Arg Asp Ser Val Lys Gly Arg Phe Thr Ile Ser Arg Asp Asn Ala Lys
        515                 520                 525

```
Asn Thr Leu Tyr Leu Gln Met Asn Ser Leu Lys Ser Glu Asp Thr Ala
        530                 535                 540
Val Tyr Tyr Cys Ala Lys Asp Pro Gly Tyr Ala Lys Gly Gln Gly
545                 550                 555                 560
Thr Gln Val Thr Val Ser Ser
                565
```

<210> SEQ ID NO 20
<211> LENGTH: 108
<212> TYPE: PRT
<213> ORGANISM: Artificial Sequence
<220> FEATURE:
<223> OTHER INFORMATION: CH1

<400> SEQUENCE: 20

```
Ala Ser Thr Lys Gly Pro Ser Val Phe Pro Leu Ala Pro Ser Ser Lys
1                   5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr
            100                 105
```

<210> SEQ ID NO 21
<211> LENGTH: 8
<212> TYPE: PRT
<213> ORGANISM: Artificial Sequence
<220> FEATURE:
<223> OTHER INFORMATION: Bevacizumab-HCDR1

<400> SEQUENCE: 21

```
Gly Tyr Thr Phe Thr Asn Tyr Gly
1               5
```

<210> SEQ ID NO 22
<211> LENGTH: 9
<212> TYPE: PRT
<213> ORGANISM: Artificial Sequence
<220> FEATURE:
<223> OTHER INFORMATION: Bevacizumab-HCDR2

<400> SEQUENCE: 22

```
Ile Asn Thr Tyr Thr Gly Glu Pro Thr
1               5
```

<210> SEQ ID NO 23
<211> LENGTH: 16
<212> TYPE: PRT
<213> ORGANISM: Artificial Sequence
<220> FEATURE:
<223> OTHER INFORMATION: Bevacizumab-HCDR3

<400> SEQUENCE: 23

```
Ala Lys Tyr Pro His Tyr Gly Ser Ser His Trp Tyr Phe Asp Val
1               5                   10                  15
```

```
<210> SEQ ID NO 24
<211> LENGTH: 6
<212> TYPE: PRT
<213> ORGANISM: Artificial Sequence
<220> FEATURE:
<223> OTHER INFORMATION: Bevacizumab-LCDR1

<400> SEQUENCE: 24

Gln Asp Ile Ser Asn Tyr
1               5

<210> SEQ ID NO 25
<211> LENGTH: 3
<212> TYPE: PRT
<213> ORGANISM: Artificial Sequence
<220> FEATURE:
<223> OTHER INFORMATION: Bevacizumab-LCDR2

<400> SEQUENCE: 25

Phe Thr Ser
1

<210> SEQ ID NO 26
<211> LENGTH: 9
<212> TYPE: PRT
<213> ORGANISM: Artificial Sequence
<220> FEATURE:
<223> OTHER INFORMATION: Bevacizumab-LCDR3

<400> SEQUENCE: 26

Gln Gln Tyr Ser Thr Val Pro Trp Thr
1               5

<210> SEQ ID NO 27
<211> LENGTH: 8
<212> TYPE: PRT
<213> ORGANISM: Artificial Sequence
<220> FEATURE:
<223> OTHER INFORMATION: Ranibizumab-HCDR1

<400> SEQUENCE: 27

Gly Tyr Asp Phe Thr His Tyr Gly
1               5

<210> SEQ ID NO 28
<211> LENGTH: 16
<212> TYPE: PRT
<213> ORGANISM: Artificial Sequence
<220> FEATURE:
<223> OTHER INFORMATION: Ranibizumab-HCDR3

<400> SEQUENCE: 28

Ala Lys Tyr Pro Tyr Tyr Tyr Gly Thr Ser His Trp Tyr Phe Asp Val
1               5                   10                  15

<210> SEQ ID NO 29
<211> LENGTH: 8
<212> TYPE: PRT
<213> ORGANISM: Artificial Sequence
<220> FEATURE:
<223> OTHER INFORMATION: HCDR1 of C-Ye-18-5 VH

<400> SEQUENCE: 29

Gly Phe Thr Phe Ser Ser Tyr Trp
1               5
```

```
<210> SEQ ID NO 30
<211> LENGTH: 8
<212> TYPE: PRT
<213> ORGANISM: Artificial Sequence
<220> FEATURE:
<223> OTHER INFORMATION: HCDR2 of C-Ye-18-5 VH

<400> SEQUENCE: 30

Ile Asn Ser Asp Ser Ser Ser Thr
1               5

<210> SEQ ID NO 31
<211> LENGTH: 8
<212> TYPE: PRT
<213> ORGANISM: Artificial Sequence
<220> FEATURE:
<223> OTHER INFORMATION: HCDR3 of C-Ye-18-5 VH

<400> SEQUENCE: 31

Ala Lys Asp Pro Gly Gly Tyr Ala
1               5
```

ANTI-VEGF-ANTI-PD-L1 BISPECIFIC ANTIBODY, PHARMACEUTICAL COMPOSITION OF SAME, AND USES THEREOF This application is a National Stage Application under 35 U.S.C. § 371 PCT/CN2021/115308, filed Aug. 30, 2021, which claims priority benefit from Chinese Patent Application No. 202010897917.1, filed on Aug. 31, 2020, the entire content of each of which is incorporated herein by reference.

The instant application contains a Sequence Listing TXT which has been submitted electronically and is hereby incorporated by reference in its entirety. Said TXT copy, created on Feb. 22, 2023, is named IEC210214PCT_SequenceListing and is 51,152 bytes in size.

TECHNICAL FIELD

The present invention belongs to the field of biomedicine, and specifically relates to an anti-VEGF-anti-PD-L1 bispecific antibody, pharmaceutical composition of the same and uses thereof.

BACKGROUND ART

Vascular endothelial growth factor (VEGF), also known as vascular permeability factor (VPF) or vascular opsonin (vasculotropin), is a highly specific homodimer protein that promotes the growth of vascular endothelial cells. VEGF family proteins include VEGF-A, VEGF-B, VEGF-C, VEGF-D, VEGF-E, VEGF-F and placental growth factor (PIGF), among which VEGF-A plays an important role in the early formation of blood vessels. In 1983, it was first isolated by Senger et al. from hepatoma cells of guinea pigs, and has functions such as increasing permeability of capillary veins and small veins, promoting division and proliferation of vascular endothelial cells, and inducing angiogenesis. At the same time, VEGF is involved in the pathogenesis and progression of many angiogenesis-dependent diseases, including cancers, some inflammatory diseases, and diabetic retinopathy. Therefore, VEGF is an important target in the research of antitumor drugs.

The main receptors of VEGF protein are VEGFR1, VEGFR2, VEGFR3, NRP1, NRP2 NRP3. However, the binding of VEGF family protein members to VEGF receptors is selective, among which VEGFA can bind to VEGFR1 and VEGFR2 to activate endogenous kinase activation and promote neovascularization. Blocking the binding of VEGF to receptor can be applied to the treatment of various cancers, such as breast cancer, colon cancer, lung cancer, ovarian cancer, endometrial cancer, mesothelioma, cervical cancer, kidney cancer (Rakesh R. Ramjiawan, Arjan W. Griffioen, and Dan G. Duda, Angiogenesis. 2017 20 (2): 185-204.).

Currently, in the global market, there are 23 marketed or approved VEGF drugs, covering 45 indications, of which bevacizumab has the most approved indications. Bevacizumab is approved in the United States, the European Union and other places for the treatment of diseases such as colorectal cancer, non-small cell lung cancer, breast cancer, malignant glioma and renal cell carcinoma. Ranibizumab is the second-generation humanized anti-VEGF recombinant mouse monoclonal antibody fragment Fab part, which is obtained from the same parental mouse antibody as Bevacizumab. The US FDA approved it on Jun. 30, 2006 for the treatment of patients with age-related macular degeneration (AMD). Compared with bevacizumab, ranibizumab maintains a better affinity for VEGFA and can better inhibit angiogenesis, and has been developed for the treatment of gastric cancer, rectal cancer and other indications.

Aflibercept is a human IgG-Fc recombinant protein composed of extracellular fragments of VEGFR1 and VEGFR2, which can simultaneously block the binding of VEGFR1 and VEGFR2 to VEGFA, thereby blocking angiogenesis of vascular epithelial cells. Aflibercept is mainly indicated for the treatment of patients with neovascular (wet) age-related macular degeneration (AMD). At the same time, it is used for the treatment of advanced bowel cancer in clinic (Caemen Stancan, etc, Rom J Morphol Embryol. 2018 59 (2): 455-467). Since aflibercept possesses functional fragments of VEGFR1 and VEGFR2, it has the function of blocking the binding of VEGF to receptor that is similar to that of antibody.

Programmed death 1 ligand 1 (PD-L1), also known as CD274, is a member of the B7 family and a ligand of PD-1. PD-L1 is a type I transmembrane protein with a total of 290 amino acids, comprising an IgV-like region, an IgC-like region, a transmembrane hydrophobic region and an intracellular region consisting of 30 amino acids. Unlike other B7 family molecules, PD-L1 negatively regulates the immune response. Studies have found that PD-L1 is mainly expressed in activated T cells, B cells, macrophages, and dendritic cells. In addition to lymphocytes, PD-L1 is also expressed in other endothelial cells of many tissues such as thymus, heart, placenta, etc., and various non-lymphoid systems such as melanoma, liver cancer, gastric cancer, renal cell carcinoma, ovarian cancer, colon cancer, breast cancer, esophageal cancer, head and neck cancer, etc. (Akintunde Akinleye & Zoaib Rasool, Journal of Hematology & Oncology volume 12, Article number: 92 (2019)). PD-L1 has a certain generality in regulating autoreactive T and B cells and immune tolerance, and plays a role in peripheral tissue T and B cell responses. High expression of PD-L1 on tumor cells is associated with poor prognosis of cancer patients.

Although bifunctional antibodies are a direction in the development of antibody drugs, they face many challenges, such as preclinical evaluation models, low expression, poor stability, complex processes, and large differences in quality control. Therefore, the development of bifunctional antibodies has always been difficult.

Therefore, it is necessary to develop a bispecific antibody against the two targets of PD-L1 and VEGF with good specificity, good curative effect and easy preparation.

CONTENTS OF THE PRESENT INVENTION

The inventors developed an anti-VEGF-anti-PD-L1 bispecific antibody (hereinafter also referred to as anti-PD-L1/VEGF bispecific antibody) through in-depth research and creative work. The inventors have surprisingly found that the anti-PD-L1/VEGF bispecific antibody of the present invention has high affinity for the dual targets of PD-L1 and VEGF, has the common biological activity of the two targets, and has a small molecular weight. It can penetrate the tumor area flexibly and has good safety. Therefore, the following invention is provided:

One aspect of the present invention relates to a bispecific antibody, which comprises:
    a first protein functional region targeting to VEGF, and
    a second protein functional region targeting to PD-L1;
    wherein:
    the first protein functional region is an anti-VEGF antibody or an antigen-binding fragment thereof, or, the first protein functional region comprises a VEGF receptor or a fragment having a VEGF receptor function;
the second protein functional region is an anti-PD-L1 single-domain antibody.

In some embodiments of the present invention, the bispecific antibody consists of the first protein functional region and the second protein functional region and an optional linker.

In some embodiments of the present invention, the bispecific antibody, wherein,
the anti-VEGF antibody has a heavy chain variable region comprising HCDR1 with an amino acid sequence as set forth in SEQ ID NO: 21, HCDR2 with an amino acid sequence as set forth in SEQ ID NO: 22, and HCDR3 with an amino acid sequence as set forth in SEQ ID NO: 23;
alternatively, the anti-VEGF antibody has a heavy chain variable region comprising HCDR1 with an amino acid sequence as set forth in SEQ ID NO: 27, HCDR2 with an amino acid sequence as set forth in SEQ ID NO: 22, and HCDR3 with an amino acid sequence as set forth in SEQ ID NO: 28;
and, the anti-VEGF antibody has a light chain variable region comprising LCDR1 with an amino acid sequence as set forth in SEQ ID NO: 24, LCDR2 with an amino acid sequence as set forth in SEQ ID NO: 25, and LCDR3 with an amino acid sequence as set forth in SEQ ID NO: 26.

The variable regions of the light chain and the heavy chain determine the binding to antigen: the variable region of each chain comprises three hypervariable regions, called complementarity determining regions (CDRs), wherein the heavy chain (H) has CDRs including HCDR1, HCDR2, HCDR3, the light chain (L) has CDRs including LCDR1, LCDR2, LCDR3. In the present invention, CDRs are defined by the IMGT numbering system, see Ehrenmann F, Kaas Q, Lefranc M P. IMGT/3Dstructure-DB and IMGT/DomainGapAlign: a database and a tool for immunoglobulins or antibodies, T cell receptors, MHC, IgSF and MhcSF[J]. Nucleic acids research, 2009; 38 (suppl_1): D301-D307.

In some embodiments of the present invention, the bispecific antibody, wherein,
the anti-PD-L1 single-domain antibody comprises a heavy chain variable region, and the heavy chain variable region comprises HCDR1 with an amino acid sequence as set forth in SEQ ID NO: 29, HCDR2 with an amino acid sequence as set forth in SEQ ID NO: 30, and HCDR3 with an amino acid sequence as set forth in SEQ ID NO: 31;
preferably, the anti-PD-L1 single-domain antibody has an amino acid sequence as set forth in SEQ ID NO: 5.

In some embodiments of the present invention, the bispecific antibody, wherein,
the anti-VEGF antibody has a heavy chain variable region with an amino acid sequence as set forth in SEQ ID NO: 3, and a light chain variable region with an amino acid sequence as set forth in SEQ ID NO: 9; or
the anti-VEGF antibody has a heavy chain variable region with an amino acid sequence as set forth in SEQ ID NO: 13, and a light chain variable region with an amino acid sequence as set forth in SEQ ID NO: 15.

In some embodiments of the present invention, the bispecific antibody, wherein,
the anti-VEGF antibody has a heavy chain variable region with an amino acid sequence as set forth in SEQ ID NO: 3, and a light chain variable region with an amino acid sequence as set forth in SEQ ID NO: 9; or
the anti-VEGF antibody has a heavy chain variable region with an amino acid sequence as set forth in SEQ ID NO: 13, and a light chain variable region with an amino acid sequence as set forth in SEQ ID NO: 15;
and, the anti-PD-L1 single-domain antibody has an amino acid sequence as set forth in SEQ ID NO: 5.

In some embodiments of the present invention, the bispecific antibody, wherein,
the anti-VEGF antibody or antigen-binding fragment thereof is selected from a group consisting of Fab, Fab', F(ab')$_2$, Fd, Fv, dAb, complementarity determining region fragment, single chain antibody, humanized antibody, chimeric antibody and double antibody.

In some embodiments of the present invention, the bispecific antibody, wherein,
the anti-VEGF antibody has a constant region derived from a human antibody;
preferably, the constant region is selected from a group consisting of constant regions of human IgG1, IgG2, IgG3 and IgG4.

In some embodiments of the present invention, the bispecific antibody, wherein,
the anti-VEGF antibody has a heavy chain constant region that is a human Ig gamma-1 chain C region or a human Ig gamma-4 chain C region, and has a light chain constant region that is human Ig kappa chain C region;
preferably, the anti-VEGF antibody has a light chain constant region with an amino acid sequence as set forth in SEQ ID NO: 10;
preferably, the anti-VEGF antibody has a light chain with an amino acid sequence as set forth in SEQ ID NO: 8 or SEQ ID NO: 14.

In some embodiments of the present invention, the bispecific antibody, wherein,
the anti-VEGF antibody has a heavy chain constant region that further comprises a L234A mutation and a L235A mutation according to EU numbering system; optionally, further comprises a G237A mutation;
preferably, the anti-VEGF antibody has a heavy chain constant region with an amino acid sequence as set forth in SEQ ID NO: 4.

In some embodiments of the present invention, the bispecific antibody, wherein:
the VEGF is VEGF-A;
the VEGF receptor is VEGFR1 and/or VEGFR2.

In some embodiments of the present invention, the bispecific antibody, wherein the single-domain antibody is ligated to the C-terminal or N-terminal of the first protein functional region, for example, there are two single-domain antibodies, one end of each single-domain antibody is ligated to the C-terminal or N-terminal of one of the two heavy chains of the anti-VEGF antibody, or to the C-terminal or N-terminal of the VEGF receptor or a fragment with VEGF receptor function:
and the single-domain antibody is ligated directly or through a linking fragment to the first protein functional region;
preferably, the linking fragment has an amino acid sequence independently selected from SEQ ID NO: 6 and SEQ ID NO: 7;
preferably, the peptide chain obtained by ligating the single-domain antibody to the first protein functional region has an amino acid sequence as set forth in SEQ ID NO: 1, SEQ ID NO: 2, SEQ ID NO: 11 or SEQ ID NO: 12.

The present invention relates to a bispecific antibody, which comprises:
a first protein functional region targeting to VEGF, and
a second protein functional region targeting to PD-L1;
wherein,
the number of the first protein functional region is 1, and the number of the second protein functional region is 2;
the first protein functional region is an anti-VEGF antibody or an antigen-binding fragment thereof, and the second protein functional region is an anti-PD-L1 single-domain antibody;
the single-domain antibody is ligated to the C-terminal of a heavy chain of the anti-VEGF antibody through a linking fragment: the peptide chain obtained after ligation has an amino acid sequence as set forth in SEQ ID NO: 1, SEQ ID NO: 2, SEQ ID NO: 11 or SEQ ID NO: 12;
the anti-VEGF antibody has a light chain with an amino acid sequence as set forth in SEQ ID NO: 8 or SEQ ID NO: 14.

In some embodiments of the present invention, the bispecific antibody, wherein,
the first protein functional region comprises: a VEGF receptor or a fragment with VEGF receptor function, and an Fc segment of IgG1;
preferably, the fragment with VEGF receptor function has an amino acid sequence as set forth in SEQ ID NO: 17;
preferably, the Fc segment of IgG1 comprises a L234A mutation and a L235A mutation according to EU numbering system:
preferably, the Fc segment of IgG1 has an amino acid sequence as set forth in SEQ ID NO: 18.

In some embodiments of the present invention, the bispecific antibody, wherein,
when the first protein functional region is a VEGF receptor or a fragment with VEGF receptor function, the bispecific antibody is a dimer: preferably, it is a dimer of a polypeptide with an amino acid sequence as set forth in SEQ ID NO: 16 or SEQ ID NO: 19.

The bispecific antibody according to any one of the items of the present invention is used for the treatment and/or prevention of a malignant tumor: preferably, the malignant tumor is selected from a group consisting of melanoma, liver cancer, gastric cancer, renal cell carcinoma, ovarian cancer, colon cancer, breast cancer, esophageal cancer and head and neck cancer.

Another aspect of the present invention relates to an isolated nucleic acid molecule, which encodes the bispecific antibody according to any one of the items of the present invention.

Another aspect of the present invention relates to a vector, which comprises the isolated nucleic acid molecule of the present invention.

Another aspect of the present invention relates to a host cell, which comprises the isolated nucleic acid molecule of the present invention, or the vector of the present invention.

Another aspect of the present invention relates to a method for preparing the bispecific antibody described in any one of the items of the present invention, which comprises steps of culturing the host cell of the present invention under suitable conditions, and recovering the bispecific antibody from the cell culture.

Another aspect of the present invention relates to a conjugate, which comprises a bispecific antibody and a coupling moiety, wherein the bispecific antibody is the bispecific antibody described in any one of the items of the present invention, and the coupling moiety is a detectable label: preferably, the coupling moiety is a radioactive isotope, a fluorescent substance, a luminescent substance, a colored substance, or an enzyme.

According to the conjugate of the present invention, it is used for the treatment and/or prevention of a malignant tumor: preferably, the malignant tumor is selected from a group consisting of melanoma, liver cancer, gastric cancer, renal cell carcinoma, ovarian cancer, colon cancer, breast cancer, esophageal cancer and head and neck cancer.

Another aspect of the present invention relates to a kit, which comprises the bispecific antibody according to any one of the items of the present invention, or comprises the conjugate of the present invention;
preferably, the kit further comprises a second antibody capable of specifically binding to the bispecific antibody; optionally, the second antibody further comprises a detectable label, such as a radioactive isotope, a fluorescent substance, a luminescent substance, a colored substance, or an enzyme.

Another aspect of the present invention relates to a use of the bispecific antibody according to any one of the items of the present invention in the manufacture of a kit, wherein the kit is used for detecting the presence or level of VEGF and/or PD-L1 in a sample.

Another aspect of the present invention relates to a pharmaceutical composition, which comprises the bispecific antibody according to any one of the items of the present invention or the conjugate of the present invention: optionally, it further comprises a pharmaceutically acceptable excipient.

Another aspect of the present invention relates to a use of the bispecific antibody according to any one of the items of the present invention or the conjugates of the present invention in the manufacture of a medicament for the prevention and/or treatment of a malignant tumor: preferably, the malignant tumor is selected from a group consisting of melanoma, liver cancer, gastric cancer, renal cell carcinoma, ovarian cancer, colon cancer, breast cancer, esophageal cancer and head and neck cancer.

Another aspect of the present invention relates to a method for treating and/or preventing a malignant tumor, comprising administering an effective amount of the bispecific antibody of any one of the items of the present invention or the conjugated antibody of the present invention to a subject in need thereof: preferably, the malignant tumor is selected from a group consisting of melanoma, liver cancer, gastric cancer, renal cell carcinoma, ovarian cancer, colon cancer, breast cancer, esophagus cancer and head and neck cancer.

In some embodiments of the present invention, the method, wherein, the step of administering an effective amount of the bispecific antibody according to any one of the items of the present invention to the subject in need thereof is before or after a surgical treatment, and/or before or after a radiation therapy.

In some embodiments of the present invention, the method, wherein,
the single administration dose of the bispecific antibody of the present invention is 0.1-100 mg, preferably 4.8-24 mg or 1-10 mg, per kilogram of body weight; or, the single administration dose of the bispecific antibody of the present invention is 10-1000 mg, preferably 50-500 mg, 100-400 mg, 150-300 mg, 150-250 mg or 200 mg, per subject;
preferably, the administration is carried out once every 3 days, 4 days, 5 days, 6 days, 10 days, 1 week, 2 weeks or 3 weeks;

preferably, the administration is carried out by a method of intravenous drip or intravenous injection.

As used herein, the term EC50 refers to a concentration for 50% of maximal effect, which refers to a concentration that can cause 50% of the maximum effect.

As used herein, the term "antibody" refers to an immunoglobulin molecule generally composed of two pairs of polypeptide chains, each pair having one "light" (L) chain and one "heavy" (H) chain. Antibody light chains can be classified as κ and λ light chains. Heavy chains can be classified as μ, δ, γ, α, or ε, and the isotypes of antibody are defined as IgM, IgD, IgG, IgA, and IgE, respectively. Within the light chain and heavy chain, variable and constant regions are linked by a "J" region of about 12 or more amino acids, and the heavy chain further comprising a "D" region of about 3 or more amino acids. Each heavy chain is composed of a heavy chain variable region (VH) and a heavy chain constant region (CH). The heavy chain constant region consists of 3 domains (CH1, CH2 and CH3). Each light chain is composed of a light chain variable region (VL) and a light chain constant region (CL). The light chain constant region consists of one domain, CL. The antibody constant regions mediate the binding of immunoglobulin to a host tissue or factor, including various cells (e.g., effector cells) of the immune system and first component (Clq) of the classical complement system. VH and VL regions can also be subdivided into regions with high variability (which are called as complementarity determining regions (CDRs)), among which more conserved regions called framework regions (FRs) are interspersed. Each VH and VL consists of 3 CDRs and 4 FRs arranged in the following order: FR1, CDR1, FR2, CDR2, FR3, CDR3, and FR4, from amino-terminal to carboxy-terminal. The variable regions (VH and VL) of each heavy chain/light chain pair form an antibody binding site, respectively. Assignment of amino acids to the regions or domains follows the definition of Bethesda M.d., Kabat Sequences of Proteins of Immunological Interest (National Institutes of Health, (1987 and 1991)), or Chothia & Lesk J. Mol. Biol. 1987:196:901-917; Chothia et al. Nature 1989:342:878-883, or the IMGT numbering system, see the definitions of Ehrenmann F, Kaas Q, Lefranc M P. IMGT/3Dstructure-DB and IMGT/DomainGapAlign: a database and a tool for immunoglobulins or antibodies, T cell receptors, MHC, IgSF and MhcSF[J]. Nucleic acids research, 2009; 38 (suppl_1): D301-D307.

The term "antibody" is not limited to any particular antibody production method. For example, it includes recombinant antibody, monoclonal antibody and polyclonal antibody. The antibody can be an antibody of different isotype, for example, IgG (e.g., IgG1, IgG2, IgG3, or IgG4 subtype), IgA1, IgA2, IgD, IgE, or IgM antibody.

As used herein, the terms "mAb" and "monoclonal antibody" refer to an antibody or a fragment of antibody derived from a group of highly homologous antibody molecules, that is, except for natural mutations that may occur spontaneously, a group of identical antibody molecules. The mAb is highly specific for a single epitope on an antigen. Compared with monoclonal antibody, a polyclonal antibody usually contains at least two or more different antibodies, and these different antibodies usually recognize different epitopes on an antigen. Monoclonal antibodies can usually be obtained using hybridoma technology that was first reported by Kohler et al. (Köhler G, Milstein C. Continuous cultures of fused cells secreting antibody of predefined specificity [J], nature, 1975; 256 (5517): 495), and can also be obtained using recombinant DNA techniques (see, for example, U.S. Pat. No. 4,816,567).

As used herein, the term "humanized antibody" refers to an antibody or an antibody fragment obtained by replacing all or part of the CDR regions of a human immunoglobulin (recipient antibody) with the CDR regions of a non-human antibody (donor antibody), wherein the donor antibody can be a non-human (e.g., mouse, rat, or rabbit) antibody with the desired specificity, affinity, or reactivity. In addition, some amino acid residues in the framework region (FR) of the recipient antibody can also be replaced by the corresponding amino acid residues of a non-human antibody, or by the amino acid residues of other antibodies, so as to further improve or optimize the performance of antibody. For more details on humanized antibodies, see, for example, Jones et al., Nature 1986:321:522 525; Reichmann et al., Nature, 1988:332:323329; Presta, Curr. Op. Struct. Biol. 1992:2:593-596; and Clark, Immunol. Today 2000; 21: 397-402. In some cases, the antigen-binding fragment of antibody is a diabody, in which the VH and VL domains are expressed on a single polypeptide chain, but the linker used is too short to allow the pairing between two domains of the same chain, thereby forcing the domain to pair with a complementary domain of another chain and creating two antigen-binding sites (see, for example, Holliger P. et al., Proc. Natl. Acad. Sci. USA 1993:90:6444 6448 and Poljak R. J. et al., Structure 1994:2:1121-1123).

The fusion protein as described herein is a protein product co-expressed by two genes through DNA recombination. Methods for producing and purifying antibodies and antigen-binding fragments are well known in the art (e.g., Cold Spring Harbor's Antibody Laboratory Technique Guide, Chapters 5-8 and Chapter 15).

As used herein, the term "isolation" or "isolated" means acquisition from a natural state by an artificial means. If an "isolated" substance or component occurs in nature, the natural environment in which it exists has been altered, or the substance has been isolated from the natural environment, or both have occurred. For example, for an unisolated polynucleotide or polypeptide naturally existing in a living animal, the same polynucleotide or polypeptide with high purity isolated from this natural state is called isolated. The term "isolation" or "isolated" does not exclude the admixture of an artificial or synthetic substance, nor the presence of other impurities which do not affect the substance activity.

As used herein, the term "vector" refers to a nucleic acid delivery vehicle into which a polynucleotide can be inserted. When the vector is capable of achieving expression of a protein encoded by the inserted polynucleotide, the vector is called an expression vector. A vector can be introduced into a host cell by transformation, transduction or transfection, so that a genetic material element it carries can be expressed in the host cell. Vectors are well known to those skilled in the art, including but not limited to: plasmid: phagemid: cosmid: artificial chromosome, such as yeast artificial chromosome (YAC), bacterial artificial chromosome (BAC) or P1-derived artificial chromosome (PAC): phage such as λ phage or M13 phage, and animal viruses. The animal viruses that can be used as vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40). A vector may contain a variety of elements that control expression, including but not limited to, promoter sequence, transcription initiation sequence, enhancer sequence, selection element, and reporter gene. In addition, the vector may also contain a replication origin.

As used herein, the term "host cell" refers to a cell that can be used to introduce a vector, including but not limited to, prokaryotic cell such as *Escherichia coli* or *Bacillus subtilis*, fungal cell such as yeast cell or *Aspergillus*, insect cell such as S2 *Drosophila* cell or Sf9, or animal cell such as fibroblast, CHO cell, GS cell, COS cell, NSO cell, HeLa cell, BHK cell, HEK293 cell or human cell.

As used herein, the term "pharmaceutically acceptable excipient" refers to a carrier and/or excipient that is pharmacologically and/or physiologically compatible with the subject and the active ingredient, which are well known in the art (see, for example, Remington's Pharmaceutical Sciences. Edited by Gennaro AR, 19th ed. Pennsylvania: Mack Publishing Company, 1995), and include but are not limited to: pH adjuster, surfactant, adjuvant, ionic strength enhancer. For example, the pH regulator includes but is not limited to phosphate buffer: the surfactant includes but is not limited to cationic, anionic or nonionic surfactant, such as Tween-80); the ionic strength enhancer includes but is not limited to sodium chloride.

As used herein, the term "effective amount" refers to an amount sufficient to achieve, or at least partially achieve, the desired effect. For example, an effective amount for preventing a disease (e.g., a tumor) refers to an amount sufficient to prevent, arrest, or delay the occurrence of a disease (e.g., a tumor): an effective amount for treating a disease refers to an amount sufficient to cure or at least partially prevent a disease and complication thereof in a patient with the disease. Determining such an effective amount is well within the capability of those skilled in the art. For example, an effective amount for therapeutic use will depend on the severity of the disease to be treated, the general state of the patient's own immune system, the general condition of the patient such as age, weight and sex, the mode of administration of drug, other therapies administered concomitantly, and so on.

In the present invention, if there is no special description, the "first" (e.g., the first protein functional region) and "second" (e.g., the second protein functional region) are used for the purpose of distinction in reference or clarity of expression, and do not have a typical sequential implication.

The present invention also relates to any one of the following items 1 to 10:

1. A bispecific antibody, characterized in that the bispecific antibody comprises:
   (a) an anti-PD-L1 single-domain antibody; and
   (b) an anti-VEGF antibody or element.

2. The bispecific antibody according to item 1, characterized in that the bispecific antibody comprises polypeptides with the structures shown in Formula I and Formula II, A1-L1-CH-L2-B    (Formula I)

A2-L3-CL    (Formula II)

wherein,
   A1 is a heavy chain variable region VH of the anti-VEGF antibody;
   A2 is a light chain variable region VL of the anti-VEGF antibody;
   B is an anti-PD-L1 single-domain antibody;
   L1, L2 and L3 are each independently none or a linking element;
   CH is a human IgG heavy chain constant region CH (preferably, LALA mutant);
   CL is a human κ light chain constant region CL; and
   "-" is a peptide bond;
   and wherein, the polypeptide represented by Formula I and the polypeptide represented by Formula II form a heterodimer through a disulfide bond interaction.

3. The bispecific antibody according to item 1, characterized in that the bispecific antibody is a polypeptide having the structure as shown in Formula III or Formula IV, A3-L4-Fc-L5-B    (Formula III)

B-L6-Fc-L7-A3    (Formula IV)

wherein,
   A3 is a domain that is capable of binding to VEGF and blocking its activity;
   B is an anti-PD-L1 single-domain antibody;
   L4, L5, L6 and L7 are each independently none or a linking element;
   Fc is an Fc region of human IgG (preferably, LALA mutant); and
   "-" is a peptide bond.

4. An isolated polynucleotide, characterized in that the polynucleotide encodes the bispecific antibody according to item 1.

5. A vector, characterized in that the vector comprises the polynucleotide according to item 4.

6. A host cell, characterized in that the host cell comprises the vector according to item 5, or the polynucleotide according to item 4 is integrated into its genome:
   alternatively, the host cell expresses the bispecific antibody according to item 1.

7. A method for producing the bispecific antibody according to item 1, characterized in comprising the steps of:
   (a) culturing the host cell according to item 6 under appropriate conditions, thereby obtaining a culture containing the bispecific antibody; and
   (b) performing purification and/or separation of the culture obtained in step (a) to obtain the bispecific antibody.

8. An immunoconjugate, characterized in that the immunoconjugate comprises:
   (a) the bispecific antibody according to item 1; and
   (b) a coupling moiety selected from a group consisting of detectable label, drug, toxin, cytokine, radionuclide, or enzyme, gold nanoparticle/nanorod, nanomagnetic particle, viral coat protein or VLP, and a combination thereof.

9. Use of the bispecific antibody according to item 1, or the immunoconjugate according to item 8, in the manufacture of a medicament, reagent, detection plate or kit: wherein, the reagent, detection plate or kit is used for: detecting PD-L1 and/or VEGF in a sample: wherein, the medicament is used for treating or preventing a tumor expressing PD-L1 (i.e., PD-L1 positive) or a tumor expressing VEGF.

10. A pharmaceutical composition, characterized in that the pharmaceutical composition comprises:
    (i) the bispecific antibody according to item 1, or the immunoconjugate according to item 8; and
    (ii) a pharmaceutically acceptable carrier.

The present invention further relates to any one of the following first to fourteenth aspects:

In the first aspect of the present invention, a bispecific antibody is provided, and the bispecific antibody comprises:
(a) an anti-PD-L1 single-domain antibody; and
(b) an anti-VEGF antibody or element.

In another preferred embodiment, the bispecific antibody comprise 1 to 3 anti-PD-L1 single domain antibodies, preferably, comprises 1 or 2 anti-PD-L1 single domain antibodies.

In another preferred embodiment, the PD-L1 single-domain antibody is capable of blocking an interaction between PD-1 and PD-L1.

In another preferred embodiment, the bispecific antibody further comprises an Fc segment.

In another preferred embodiment, the Fc segment of the bispecific antibody is selected from a group consisting of human IgG domain, CH1+CL1 domain, and a combination thereof.

In another preferred embodiment, the human IgG domain is a modified mutant IgG domain, preferably a LALA mutant IgG domain.

In another preferred embodiment, the bispecific antibody comprises polypeptides with the structures shown in Formula I and Formula II, A1-L1-CH-L2-B        (Formula I)

A2-L3-CL             (Formula II)

wherein,

A1 is a heavy chain variable region VH of the anti-VEGF antibody;

A2 is a light chain variable region VL of the anti-VEGF antibody;

B is an anti-PD-L1 single-domain antibody;

L1, L2 and L3 are each independently none or a linking element;

CH is a human IgG heavy chain constant region CH (preferably, LALA mutant);

CL is a human κ light chain constant region CL; and

"-" is a peptide bond;

and wherein, the polypeptide represented by Formula I and the polypeptide represented by Formula II form a heterodimer through a disulfide bond interaction.

In another preferred embodiment, the bispecific antibody is a polypeptide having a structure as shown in Formula III or Formula IV, A3-L4-Fc-L5-B        (Formula III)

B-L6-Fc-L7-A3        (Formula IV)

wherein,

A3 is a domain capable of binding to VEGF and blocking its activity;

B is an anti-PD-L1 single-domain antibody;

L4, L5, L6 and L7 are each independently none or a linking element;

Fc is an Fc region of human IgG (preferably, LALA mutant); and

"-" is a peptide bond.

In another preferred embodiment, the anti-VEGF heavy chain variable region VH has a heavy chain variable region amino acid sequence derived from Bevacizumab, and the amino acid sequence is set forth in SEQ ID NO: 3, or has ≥85% (preferably 90%, more preferably 95%) sequence identity with the sequence set forth in SEQ ID NO: 3.

In another preferred embodiment, the anti-VEGF light chain variable region VL has a light chain variable region amino acid sequence derived from Bevacizumab, and the amino acid sequence is set forth in SEQ ID NO: 9, or has ≥85% (preferably 90%, more preferably 95%) sequence identity with the sequence set forth in SEQ ID NO: 9.

In another preferred embodiment, the anti-VEGF heavy chain variable region VH has a heavy chain variable region amino acid sequence derived from Ranibizumab, and the amino acid sequence is set forth in SEQ ID NO: 13, or has ≥85% (preferably 90%, more preferably 95%) sequence identity with the sequence set forth in SEQ ID NO: 13.

In another preferred embodiment, the anti-VEGF light chain variable region VL has a light chain variable region amino acid sequence derived from Ranibizumab, and the amino acid sequence is set forth in SEQ ID NO: 15, or has ≥85% (preferably 90%, more preferably 95%) sequence identity with the sequence set forth in SEQ ID NO: 15.

In another preferred embodiment, the domain capable of binding to VEGF and blocking its activity has an amino acid sequence that is set forth in SEQ ID NO: 17, or has ≥85% (preferably 90%, more preferably 95%) sequence identity with the sequence set forth in SEQ ID NO: 17.

In another preferred embodiment, the anti-PD-L1 single-domain antibody has an amino acid sequence that is set forth in SEQ ID NO: 5, or has >85% (preferably 90%, more preferably 95%) sequence identity with the sequence set forth in SEQ ID NO: 5.

In another preferred embodiment, the human IgG heavy chain constant region CH has a LALA mutation with an amino acid sequence that is set forth in SEQ ID NO: 4, or has ≥85% (preferably 90%, more preferably 95%) sequence identity with the sequence set forth in SEQ ID NO: 4.

In another preferred embodiment, the human κ light chain constant region CL has an amino acid sequence that is as set forth in SEQ ID NO: 10, or has ≥85% (preferably 90%, more preferably 95%) sequence identity with the sequence set forth in SEQ ID NO: 10.

In another preferred embodiment, the Fc segment of human IgG has a LALA mutation with an amino acid sequence that is set forth in SEQ ID NO: 18, or has ≥85% (preferably 90%, more preferably 95%) sequence identity with the sequence set forth in SEQ ID NO: 18.

In another preferred embodiment, the linker element has a sequence of (G4S) n, wherein n is a positive integer (e.g., 1, 2, 3, 4, 5 or 6), preferably, n is 2 or 4.

In another preferred embodiment, the linker element has an amino acid sequence that is set forth in SEQ ID NO: 6 or 7, or has ≥85% (preferably 90%, more preferably 95%) sequence identity with the sequence set forth in SEQ ID NO: 6 or 7.

In another preferred embodiment, the bispecific antibody comprises polypeptides having the structures shown in Formula I and Formula II, wherein the polypeptide having the structure shown in Formula I has an amino acid sequence set forth in SEQ ID NO: 1, and the polypeptide having the structure shown in Formula II has an amino acid sequence set forth in SEQ ID NO: 8, namely Ava-2GS-NSD).

In another preferred embodiment, the bispecific antibody comprises polypeptides having the structures shown in Formula I and Formula II, wherein the polypeptide having the structure shown in Formula I has an amino acid sequence set forth in SEQ ID NO: 2, and the polypeptide having the structure shown in Formula II has an amino acid sequence set forth in SEQ ID NO: 8, namely Ava-4GS-NSD).

In another preferred embodiment, the bispecific antibody comprises polypeptides having the structures shown in Formula I and Formula II, wherein the polypeptide having the structure shown in Formula I has an amino acid sequence set forth in SEQ ID NO: 11, and the polypeptide having the structure shown in Formula II has an amino acid sequence set forth in SEQ ID NO: 14, namely Luc-2GS-NSD).

In another preferred embodiment, the bispecific antibody comprises polypeptides having the structures shown in Formula I and Formula II, wherein the polypeptide having the structure shown in Formula I has an amino acid sequence set forth in SEQ ID NO: 12, and the polypeptide having the structure shown in Formula II has an amino acid sequence set forth in SEQ ID NO: 14, namely Luc-4GS-NSD).

In another preferred embodiment, the bispecific antibody is a polypeptide having the structure shown in Formula III, and its amino acid sequence is set forth in SEQ ID NO: 16, namely NSD-Elyea).

In another preferred embodiment, the bispecific antibody is a polypeptide having the structure shown in Formula III, and its amino acid sequence is set forth in SEQ ID NO: 19, namely Elyea-NSD).

In another preferred embodiment, the bispecific antibody comprises at the same time polypeptides of the structures shown in Formula I and Formula II, and the polypeptide shown in Formula I and the polypeptide shown in Formula II form a heterodimer i through a disulfide bond action:

and, the heterodimers i form a homodimer ii through a disulfide bond interaction between CH domains.

In another preferred embodiment, the bispecific antibody is a polypeptide having the structure shown in Formula III or Formula IV, and the polypeptides with the structure shown in Formula III or Formula IV form a homodimer through a disulfide bond action between Fc segments.

In the second aspect of the present invention, an isolated polynucleotide encoding the bispecific antibody according to the first aspect of the present invention is provided.

In another preferred embodiment, when the bispecific antibody comprises polypeptides with structures shown in Formula I and Formula II, in the polynucleotide, the polynucleotide sequence encoding the polypeptide of the structure shown in Formula I and the polynucleotide sequence encoding the polypeptide of the structure shown in Formula II are in a ratio of 1:1.

In the third aspect of the present invention, a vector containing the polynucleotide according to the second aspect of the present invention is provided.

In another preferred embodiment, the vector is selected from a group consisting of DNA, RNA, viral vector, plasmid, transposon, other gene transfer system, and a combination thereof: preferably, the expression vector includes viral vector, such as lentivirus, adenovirus, AAV virus, retrovirus, or a combination thereof.

In the fourth aspect of the present invention, a host cell is provided, wherein the host cell comprises the vector according to the third aspect of the present invention, or the polynucleotide according to the second aspect of the present invention is integrated in its genome:

alternatively, the host cell expresses the bispecific antibody according to the first aspect of the present invention.

In another preferred embodiment, the host cell includes prokaryotic cell or eukaryotic cell In another preferred embodiment, the host cell is selected from a group consisting of *Escherichia coli*, yeast cell, and mammalian cell.

In the fifth aspect of the present invention, there is provided a method for producing the bispecific antibody according to the first aspect of the present invention, comprising the steps of:
(a) cultivating the host cell according to the fourth aspect of the present invention under suitable conditions, so as to obtain a culture containing the bispecific antibody; and
(b) performing purification and/or separation of the culture obtained in step (a) to obtain the bispecific antibody.

In another preferred embodiment, the purification can be performed by protein A affinity column purification and separation to obtain the target antibody.

In another preferred embodiment, the target antibody after the purification and separation has a purity of greater than 95%, greater than 96%, greater than 97%, greater than 98%, greater than 99%, preferably 100%.

In the sixth aspect of the present invention, an immunoconjugate is provided, which comprises:
(a) the bispecific antibody according to the first aspect of the present invention; and
(b) a coupling moiety selected from a group consisting of detectable label, drug, toxin, cytokine, radionuclide, or enzyme, gold nanoparticle/nanorod, nanomagnetic particle, viral coat protein or VLP, and a combination thereof.

In another preferred embodiment, the radionuclide includes:
(i) an isotope for diagnosis, in which the isotope for diagnosis is selected from a group consisting of Tc-99m, Ga-68, F-18, I-123, I-125, I-131, In-111, Ga-67, Cu-64, Zr-89, C-11, Lu-177, Re-188, and a combination thereof; and/or
(ii) a therapeutic isotope, in which the therapeutic isotope is selected from a group consisting of Lu-177, Y-90, Ac-225, As-211, Bi-212, Bi-213, Cs-137, Cr-51, Co-60, Dy-165, Er-169, Fm-255, Au-198, Ho-166, 1-125, I-131, Ir-192, Fe-59, Pb-212, Mo-99, Pd-103, P-32, K-42, Re-186, Re-188, Sm-153, Ra223, Ru-106, Na24, Sr89, Tb-149, Th-227, Xe-133 Yb-169, Yb-177, and a combination thereof.

In another preferred embodiment, the coupling moiety is a drug or a toxin.

In another preferred embodiment, the drug is a cytotoxic drug.

In another preferred embodiment, the cytotoxic drug is selected from a group consisting of anti-tubulin drug, DNA minor groove binding agent, DNA replication inhibitor, alkylating agent, antibiotic, folic acid antagonist, antimetabolite, chemotherapy sensitizer, topoisomerase inhibitor, *vinca* alkaloid, and a combination thereof.

Examples of particularly useful classes of cytotoxic drug include, for example, DNA minor groove binding agent, DNA alkylating agent, and tubulin inhibitor. Typical cytotoxic drugs include, for example, auristatins, camptothecins, duocarmycins, etoposides, maytansines and maytansinoids (e.g., DM1 and DM4), taxanes, benzodiazepines, or benzodiazepine-containing drug (e.g., pyrrolo[1,4]benzodiazepines (PBDs), indolinobenzodiazepines and oxazolidinobenzodiazepines), *vinca* alkaloids, or a combination thereof.

In another preferred embodiment, the toxin is selected from a group consisting of:
auristatins (e.g., auristatin E, auristatin F, MMAE, and MMAF), aureomycin, maytansinoids, ricin, ricin A-chain, combretastatin, duocarmycin, dolastatin, doxorubicin, daunorubicin, paclitaxel, cisplatin, cc1065, ethidium bromide, mitomycin, etoposide, tenoposide, vincristine, vinblastine, colchicine, dihydroxyanthracindione, actinomycin, diphtheria toxin, *Pseudomonas* exotoxin (PE) A, PE40, abrin, abrin A chain, modeccin A chain, α-Sarcina, gelonin, mitogellin, retstrictocin, phenomycin, enomycin, curicin, crotin, calicheamicin, *Sapaonaria officinalis* inhibitor, glucocorticoid, and a combination thereof.

In another preferred embodiment, the coupling moiety is a detectable label.

In another preferred embodiment, the conjugate is selected from a group consisting of: fluorescent or luminescent label, radioactive label, MRI (magnetic resonance imaging) or CT (computer X-ray tomography) contrast agent, or enzyme capable of producing detectable product, radionuclide, biotoxin, cytokine (e.g., IL-2), antibody, antibody Fc fragment, antibody scFv fragment, gold nanoparticle/nanorod, virus particle, liposome, nanomagnetic particle, prodrug-activating enzyme (e.g., DT-diaphorase (DTD) or biphenylhydrolase-like protein (BPHL)), and chemotherapeutic agent (e.g., cisplatin).

In another preferred embodiment, the immunoconjugate comprises: a multivalent (e.g., bivalent) bispecific antibody as described in the first aspect of the present invention.

In another preferred embodiment, the multivalent refers to that the bispecific antibody according to the first aspect of the present invention comprises multiple repeats of the amino acid sequence of the immunoconjugate.

In the seventh aspect of the present invention, there is provided a use of the bispecific antibody according to the first aspect of the present invention, or the immunoconjugate according to the sixth aspect of the present invention, in the manufacture of a medicament, reagent, detection plate or kit: wherein, the reagent, detection plate or kit is used for: detecting PD-L1 and/or VEGF in a sample: wherein, the medicament is used for treating or preventing a tumor expressing PD-L1 (i.e., PD-L1 positive) or a tumor expressing VEGF.

In another preferred embodiment, the coupling moiety of the immunoconjugate is an isotope for diagnosis.

In another preferred embodiment, the reagent is one or more reagents selected from a group consisting of: isotopic tracer, contrast agent, flow detection reagent, cellular immunofluorescence detection reagent, magnetic nanoparticle and imaging agent.

In another preferred embodiment, the reagent for detecting PD-L1 and/or VEGF in the sample is a contrast agent for detecting PD-L1 and/or VEGF molecules (in vivo).

In another preferred embodiment, the detection is an in vivo detection or an in vitro detection.

In another preferred embodiment, the detection includes flow detection and cell immunofluorescence detection.

In another preferred embodiment, the agent is used for blocking an interaction between PD-1 and PD-L1, and at the same time blocking an interaction between VEGF and VEGFR.

In another preferred embodiment, the tumor includes but is not limited to: acute myeloid leukemia, chronic myelogenous leukemia, multiple myelopathy, non-Hodgkin's lymphoma, colorectal cancer, breast cancer, colorectal cancer, gastric cancer, liver cancer, leukemia, kidney tumor, lung cancer, small intestine cancer, bone cancer, prostate cancer, prostate cancer, cervical cancer, lymphoma, adrenal gland tumor, bladder tumor.

In the eighth aspect of the present invention, a pharmaceutical composition is provided, which comprises:
(i) the bispecific antibody according to the first aspect of the present invention, or the immunoconjugate according to the sixth aspect of the present invention; and
(ii) a pharmaceutically acceptable carrier.

In another preferred embodiment, the coupling moiety of the immunoconjugate is a drug, a toxin, and/or a therapeutic isotope.

In another preferred embodiment, the pharmaceutical composition further comprises an additional drug for treating tumor, such as a cytotoxic drug.

In another preferred embodiment, the additional drug for treating tumor includes paclitaxel, doxorubicin, cyclophosphamide, axitinib, lenvatinib, and pembrolizumab.

In another preferred embodiment, the drug is used for blocking an interaction between PD-1 and PD-L1, and at the same time blocking an interaction between VEGF and VEGFR.

In another preferred embodiment, the pharmaceutical composition is used for blocking PD-1/PD-L1 and/or VEGF/VEGFR signaling pathways.

In another preferred embodiment, the pharmaceutical composition is used for treating a tumor expressing PD-L1 protein (i.e., PD-L1 positive) and/or expressing VEGF protein (i.e., VEGF positive).

In another preferred embodiment, the pharmaceutical composition is in the form of injection.

In another preferred embodiment, the pharmaceutical composition is used in the manufacture of a medicament for preventing and treating a tumor.

In the ninth aspect of the present invention, there is provided one or more uses of the bispecific antibody according to the first aspect of the present invention selected from a group consisting of:
(i) use for detecting a human PD-L1 molecule and/or a VEGF molecule: (ii) use for flow detection: (iii) use for cell immunofluorescence detection: (iv) use for treating a tumor: (v) use for tumor diagnosis: (vi) use for blocking an interaction between PD-1 and PD-L1; and (vii) use for blocking an interaction between VEGF and VEGFR.

In another preferred embodiment, the tumor is a tumor expressing PD-L1 protein (i.e., PD-L1 positive) and/or expressing VEGF protein (i.e., VEGF positive).

In another preferred embodiment, the use is a non-diagnostic and non-therapeutic use.

In the tenth aspect of the present invention, a recombinant protein is provided, in which the recombinant protein has: (i) the bispecific antibody according to the first aspect of the present invention; and (ii) optionally, a tag sequence capable of assisting in expression and/or purification.

In another preferred embodiment, the tag sequence includes 6His tag, HA tag and Fc tag.

In another preferred embodiment, the recombinant protein specifically binds to PD-L1 and/or VEGF.

In the eleventh aspect of the present invention, there is provided a method for detecting PD-L1 and/or VEGF in a sample, the method comprising the steps of: (1) contacting the sample with the bispecific antibody according to the first aspect of the present invention: (2) detect whether an antigen-antibody complex is formed, wherein the formation of the complex indicates the presence of PD-L1 and/or VEGF in the sample.

In the twelfth aspect of the present invention, there is provided a method for treating a disease, the method comprising: administering the bispecific antibody according to the first aspect of the present invention, or the immunoconjugate according to the sixth aspect of the present invention, or the pharmaceutical composition according to the eighth aspect of the present invention to a subject in need thereof.

In another preferred embodiment, the subject comprises a mammal, preferably a human.

In the thirteenth aspect of the present invention, a PD-L1 and/or VEGF detection reagent is provided, the detection reagent comprises the immunoconjugate according to the sixth aspect of the present invention and a detection-acceptable carrier.

In another preferred embodiment, the coupling moiety of the immunoconjugate is an isotope for diagnosis.

In another preferred embodiment, the detection-acceptable carrier is a non-toxic, inert aqueous carrier medium.

In another preferred embodiment, the detection reagent is one or more reagents selected from a group consisting of: isotopic tracer, contrast agent, flow detection reagent, cellular immunofluorescence detection reagent, magnetic nanoparticle and imaging agent.

In another preferred embodiment, the detection reagent is used for in vivo detection.

In another preferred embodiment, the detection reagent is in the dosage form of liquid or powder (e.g., aqueous solution, injection, freeze-dried powder, tablet, buccal preparation, inhalable aerosol).

In the fourteenth aspect of the present invention, a kit for detecting PD-L1 and/or VEGF is provided, the kit comprises the immunoconjugate according to the sixth aspect of the present invention or the detection reagent according to the thirteenth aspect of the present invention, and an instruction.

In another preferred embodiment, the instruction describes that the kit is useful in the non-invasive detection of the expression of PD-L1 and/or VEGF in a subject.

In another preferred embodiment, the kit is useful in the detection of a tumor expressing PD-L1 protein (i.e., PD-L1 positive) and/or VEGF protein (i.e., VEGF positive).

Terms

In order that the present disclosure may be more readily understood, certain terms are first defined. As used in the present application, unless expressly stated otherwise herein, each of the following terms shall have the meaning given below. Other definitions are set forth throughout the present application.

Bispecific Antibody

As used herein, the terms "bispecific antibody of the present invention", "double antibody of the present invention", and "anti-PD-L1/VEGF bispecific antibody" have the same meaning, and they all refer to a bispecific antibody capable of specifically recognizing and binding to PD-L1 and VEGF. For the protein functional region with VEGF-binding activity, when it is a VEGF receptor (e.g., VEGFR1 and/or VEGFR2) or functional fragment thereof, since it has the function of blocking the binding of VEGF to receptor similar to that of antibody, the fusion protein in this case is also broadly referred to as a bispecific antibody in the present invention.

The present invention provides an anti-PD-L1/VEGF bispecific antibody, which comprises: an anti-PD-L1 single-domain antibody and an anti-VEGF antibody or element.

Preferably, the bispecific antibody comprises polypeptides with the structures shown in Formula I and Formula II, A1-L1-CH-L2-B (Formula I)

A2-L3-CL (Formula II)

wherein,
A1 is a heavy chain variable region VH of the anti-VEGF antibody;
A2 is a light chain variable region VL of the anti-VEGF antibody;
B is an anti-PD-L1 single-domain antibody;
L1, L2 and L3 are each independently none or a linking element;
CH is a human IgG heavy chain constant region CH (preferably, LALA mutant);
CL is a human κ light chain constant region CL; and
"-" is a peptide bond;
and wherein, the polypeptide represented by Formula I and the polypeptide represented by Formula II form a heterodimer through a disulfide bond interaction.

Alternatively, the bispecific antibody is a polypeptide having the structure as shown in Formula III or Formula IV, A3-L4-Fc-L5-B (Formula III)

B-L6-Fc-L7-A3 (Formula IV)

wherein,
A3 is a domain capable of binding to VEGF and blocking its activity;
B is an anti-PD-L1 single-domain antibody;
L4, L5, L6 and L7 are each independently none or a linking element;
Fc is an Fc region of human IgG (preferably, LALA mutant); and
"-" is a peptide bond.

In one embodiment, the bispecific antibody comprises at the same time polypeptides of the structures shown in Formula I and Formula II, and the polypeptide shown in Formula I and the polypeptide shown in Formula II form a heterologous dimer i;
furthermore, the heterodimers i form a homodimer ii through a disulfide bond interaction between CH domains.

In another embodiment, the bispecific antibody is a polypeptide having the structure shown in Formula III or Formula IV, and the polypeptides having the structure shown in Formula III or Formula IV form a homodimer through a disulfide bond interaction between Fc segments.

As used herein, the terms "single-domain antibody", "nanobody VHH", and "nanobody" have the same meaning and refer to a nanobody consisting of only one heavy chain variable region (VHH) constructed by cloning the antibody heavy chain variable region, which is the smallest antigen-binding fragment with complete function. Usually, after an antibody naturally lacking light chain and heavy chain constant region 1 (CH1) is obtained, and then the antibody heavy chain variable region is cloned to construct a nanobody (VHH) consisting of only one heavy chain variable region.

As used herein, the term "variable" means that certain portions of antibody variable regions differ in sequence, which contribute to the binding and specificity of each particular antibody for its particular antigen. However, the variability is not evenly distributed throughout antibody variable domains. It is concentrated in three segments called complementarity determining regions (CDRs) or hypervariable regions in the light chain and heavy chain variable regions. The more conserved portions of the variable domains are called framework regions (FRs). The variable regions of native heavy and light chains each contain four FR regions that are in an approximate B-folded configuration and connected by three CDRs that form joining loops, which in some cases may form a partially B-folded structure. The CDRs in each chain are brought into close proximity by the FR regions and together with the CDRs of the other chain form the antigen-binding site of the antibody (see Kabat et al., NIH Publ. No. 91-3242, Vol. I, pp. 647-669 (1991)). The constant regions are not directly involved in the binding of antibody to antigen, but they exhibit different effector functions, for example being involved in the antibody-dependent cytotoxicity of antibody.

As used herein, the term "framework region" (FR) refers to an amino acid sequence inserted between CDRs, i.e., a portion of immunoglobulin light and heavy chain variable regions that is relatively conservative among different immunoglobulins in a single species. Each of immunoglobulin light and heavy chains has four FRs, referred to as FR1-L, FR2-L, FR3-L, FR4-L and FR1-H, FR2-H, FR3-H, FR4-H, respectively. Accordingly, the light chain variable domain may thus be referred to as (FR1-L)-(CDR1-L)-(FR2-L)-(CDR2-L)-(FR3-L)-(CDR3-L)-(FR4-L) and the heavy chain variable domain can thus be expressed as (FR1-H)-(CDR1-H)-(FR2-H)-(CDR2-H)-(FR3-H)-(CDR3-H)-(FR4-H). Preferably, the FR of the present invention is a human antibody FR or a derivative thereof, and the human antibody FR derivative is substantially identical to the naturally occurring human antibody FR, that is, the sequence identity reaches 85%, 90%, 95%, or 96%., 97%, 98%, or 99%.

Knowing the amino acid sequences of CDRs, those skilled in the art can easily determine the framework regions FR1-L, FR2-L, FR3-L, FR4-L and/or FR1-H, FR2-H, FR3-H, FR4-H.

As used herein, the term "human framework region" is a framework region that is substantially (about 85% or more, specifically 90%, 95%, 97%, 99% or 100%) identical to a naturally occurring human antibody framework region.

As used herein, the term "affinity" is theoretically defined by the equilibrium association between intact antibody and antigen. The affinity of the bispecific antibody of the present invention can be evaluated or determined by KD value (dissociation constant) or other measurement methods, for example, determined by bio-layer interferometry (BLI) using FortebioRed96 instrument.

As used herein, the term "linker" refers to one or more amino acid residues inserted into immunoglobulin domain to provide sufficient mobility for the domains of light and heavy chains to fold into an immunoglobulin with exchanged dual variable regions.

As known to those skilled in the art, immunoconjugates and fusion expression products include conjugates formed by binding a drug, toxin, cytokine, radionuclide, enzyme and other diagnostic or therapeutic molecules to the antibody or fragment thereof of the present invention. The present invention also comprises a cell surface marker or antigen that binds to the PD-L1/VEGF bispecific antibody or fragment thereof.

As used herein, the terms "variable region" and "complementarity determining region (CDR)" are used interchangeably.

In a preferred embodiment of the present invention, the heavy chain variable region of the antibody comprises three complementarity determining regions, CDR1, CDR2 and CDR3.

In a preferred embodiment of the present invention, the heavy chain of the antibody comprises the above-mentioned heavy chain variable region and heavy chain constant region.

In the present invention, the terms "antibody of the present invention", "protein of the present invention", or "polypeptide of the present invention" are used interchangeably, and all refer to a polypeptide that specifically binds to PD-L1 and/or VEGF protein, for example, a protein or polypeptide having the heavy chain variable regions. They may or may not contain starting methionine.

The present invention further provides another protein or fusion expression product having the antibody of the present invention. Specifically, the present invention comprises any protein or protein conjugate and fusion expression product (i.e., immunoconjugate and fusion expression product) having a heavy chain containing a variable region, as long as the variable region is identical or at least 90% homologous, preferably at least 95% homologous to the heavy chain variable region of the antibody of the present invention.

In general, the antigen-binding properties of an antibody can be described by 3 specific regions located in a heavy chain variable region, which are called CDRs and separated the segment into 4 framework regions (FRs), and the amino acid sequences of the 4 FRs are relatively conservative and do not directly participate in the binding reaction. These CDRs form a ring structure, and the β folds formed by the FRs therebetween are close to each other in the spatial structure, and the CDRs on heavy chain and the corresponding CDRs on light chain constitute the antigen-binding site of the antibody. By comparing the amino acid sequences of antibodies of the same type, it is possible to determine which amino acids constitute FR or CDR regions.

The variable regions of the heavy chains of the antibody of the present invention are of particular interest, because at least some of them are involved in the binding to antigen. Therefore, the present invention comprises those molecules having an antibody heavy chain variable region with a CDR, as long as the CDR is more than 90% (preferably more than 95%, and most preferably more than 98%) homologous to the CDR identified herein.

The present invention comprises not only an intact antibody, but also an antibody fragment with immunological activity or a fusion protein formed with the antibody and other sequences. Accordingly, the present invention further comprises fragments, derivatives and analogs of the antibody.

As used herein, the terms "fragment", "derivative" and "analogue" refer to a polypeptide that substantially retains the same biological function or activity of the antibody of the present invention. The polypeptide fragment, derivative or analog of the present invention may be (i) a polypeptide having one or more substituted conservative or non-conservative amino acid residues (preferably conservative amino acid residues), and such substituted amino acid residues may or may not be encoded by genetic code, or (ii) a polypeptide having a substituent group in one or more amino acid residues, or (iii) a polypeptide formed by fusing a mature polypeptide to another compound (e.g., a compound that extends the half-life of the polypeptide, for example, polyethylene glycol), or (iv) a polypeptide formed by fusing an additional amino acid sequence to a polypeptide sequence (e.g., a fusion protein formed by a leader sequence or a secretory sequence or a sequence or proprotein sequence for purifying the polypeptide, or by a 6His tag). In light of the teachings herein, such fragment, derivative and analog are within the purview of those skilled in the art.

The antibody of the present invention refers to a double antibody with activity of binding to PD-L1 and/or VEGF protein. The term also refers to a polypeptide variant comprising the same CDR regions and having the same function as the antibody of the present invention. Such variant form includes (but is not limited to): deletion, insertion and/or substitution of one or more (usually 1-50, preferably 1-30, more preferably 1-20, and most preferably 1-10) amino acids, and addition of one or several (usually within 20, preferably within 10, more preferably within 5) amino acids at C-terminal and/or N-terminal. For example, in the art, substitution of amino acid with closer or similar properties generally does not change the function of protein. As another example, addition of one or several amino acids at C-terminal and/or N-terminal usually does not change the function of protein. The term further refers to an active fragment and active derivative of the antibody of the present invention.

Variants of the polypeptide include: homologous sequence, conservative variant, allelic variant, natural mutant, induced mutant, protein encoded by a DNA capable of hybridizing to the DNA of the antibody of the present invention under highly or lowly stringent conditions, and polypeptide or protein obtained by using the antiserum against the antibody of the present invention.

The present invention further provides other polypeptides, such as fusion proteins comprising single domain antibodies or fragments thereof. In addition to substantially full-length polypeptides, the present invention further comprises fragments of the single domain antibodies of the present invention. Typically, the fragment has at least about 50 contiguous amino acids, preferably at least about 50 contiguous amino acids, more preferably at least about 80 contiguous amino acids, and most preferably at least about 100 contiguous amino acids of the antibody of the present invention.

In the present invention, "conservative variant of the antibody of the present invention" refers to a polypeptide formed by substitution of at most 10, preferably at most 8, more preferably at most 5, and most preferably at most 3 amino acid sequences with amino acids with similar or closer properties as compared with the amino acid sequence of the antibody of the present invention. These conservative variant polypeptides are preferably produced by amino acid substitutions according to Table A.

TABLE A

| Original residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention further provides a polynucleotide molecule encoding the above-mentioned antibody or fragment thereof or fusion protein thereof. The polynucleotide of the present invention may be in the form of DNA or RNA. The form of DNA comprises cDNA, genomic DNA or synthetic DNA. The DNA can be single-stranded or double-stranded. The DNA can be either a coding strand or a non-coding strand.

The polynucleotide encoding the mature polypeptide of the present invention comprises: a coding sequence that encodes only the mature polypeptide: a coding sequence for the mature polypeptide and various additional coding sequences: a coding sequence for the mature polypeptide (and optional additional coding sequences) and non-coding sequences.

The term "polynucleotide encoding polypeptide" may include a polynucleotide encoding the polypeptide, or may also include an additional coding and/or non-coding sequence.

The present invention further relates to a polynucleotide that hybridizes to the above-mentioned sequence and has at least 50%, preferably at least 70%, more preferably at least 80% identity between the two sequences. The present invention particularly relates to a polynucleotide which is hybridizable under stringent conditions to the polynucleotide of the present invention. In the present invention, "stringent conditions" refer to: (1) hybridization and elution at lower ionic strength and higher temperature, for example, 0.2×SSC, 0.1% SDS, 60° C.; or (2) hybridization in the presence of a denaturing agent, for example, 50% (v/v) formamide, 0.1% calf serum/0.1% Ficoll, 42° C., etc.; or (3) hybridization that occurs only when the identity between two sequences is at least 90%, preferably more than 95%. Moreover, the polypeptide encoded by the hybridizable polynucleotide has the same biological function and activity as the mature polypeptide.

The full-length nucleotide sequence of the antibody of the present invention or its fragment can usually be obtained by PCR amplification, recombination or artificial synthesis. A feasible method is to use artificial synthesis to synthesize related sequences, especially when the fragment length is short. Usually, a fragment with very long sequence is obtained by synthesizing multiple small fragments and then ligating them. In addition, a fusion protein may also be formed by fusing the coding sequence of heavy chain with an expression tag (e.g., 6His).

Once a relevant sequence is obtained, a recombinant method can be used to obtain the relevant sequences in large quantity. Usually, it is cloned into a vector, then transformed into a cell, and then the relevant sequence is isolated from the proliferated host cell by conventional methods. The biomolecules (nucleic acid, protein, etc.) involved in the present invention include biomolecules in isolated form.

At present, the DNA sequence encoding the protein of the present invention (or its fragment, or its derivative) can be obtained completely through chemical synthesis. The DNA sequence can then be introduced into various existing DNA molecules (e.g., vectors) and cells known in the art. In addition, a mutation can also be introduced into the protein sequence of the present invention by chemical synthesis.

The present invention also relates to a vector comprising the above-mentioned appropriate DNA sequence and appropriate promoter or control sequence. These vectors can be used to transform appropriate host cells so that they express the protein.

The host cell may be a prokaryotic cell, such as bacterial cell: or lower eukaryotic cell, such as yeast cell: or a higher eukaryotic cell, such as a mammalian cell. Representative examples are: *Escherichia coli, Streptomyces*: bacterial cell such as *Salmonella typhimurium*: fungal cell such as yeast: insect cell such as *Drosophila* S2 or Sf9: animal cell such as CHO, COS7, 293 cell, etc.

Transformation of host cells with recombinant DNA can be performed using conventional techniques well known to those skilled in the art. When the host is a prokaryotic organism such as *Escherichia coli*, competent cells capable of taking up DNA can be harvested after the exponential growth phase and treated with CaCl2 using procedures well known in the art. Another way is to use MgCl2. The transformation can also be performed by electroporation, if desired. When the host is a eukaryotic organism, the following DNA transfection methods can be used: calcium phosphate co-precipitation method, conventional mechanical methods such as microinjection, electroporation, liposome packaging, etc.

The obtained transformant can be cultured by conventional methods to express the polypeptide encoded by the gene of the present invention. The medium used in the culture can be selected from various conventional media according to the host cells as used. The culture is carried out under conditions suitable for the growth of the host cell. After the host cell has grown to an appropriate cell density, the selected promoter is induced by an appropriate method (e.g., temperature shift or chemical induction), and the cells are cultured for an additional period of time.

The recombinant polypeptide in the above method can be expressed inside the cell, or on the cell membrane, or secreted outside the cell. The recombinant protein can be isolated and purified by various separation methods by taking advantage of its physical, chemical, and other properties, if desired. These methods are well known to those skilled in the art. Examples of these methods include, but are not limited to: conventional renaturation treatment, treatment with protein precipitating agent (salting out method), centrifugation, osmotic disruption, supertreatment, ultracentrifugation, molecular sieve chromatography (gel filtration), adsorption chromatography, ion exchange chromatography, high performance liquid chromatography (HPLC) and various other liquid chromatography techniques and combinations of these methods.

The antibody of the present invention can be used alone, or combined or conjugated with a detectable label (for diagnostic purposes), a therapeutic agent, a PK (protein kinase) modifying moiety, or a combination of any of these substances.

The detectable label for diagnostic purposes includes, but is not limited to, fluorescent or luminescent label, radioactive label, MRI (magnetic resonance imaging) or CT (computed tomography) contrast agent, or enzyme capable of producing a detectable product.

The therapeutic agent that can be combined or conjugated with the antibody of the present invention includes, but is not limited to: 1. radionuclide: 2. biological toxicity: 3. cytokine such as IL-2, etc.: 4. gold nanoparticle/nanorod: 5. virus: 6. liposome: 7. nanomagnetic particle: 8. prodrug-activating enzyme (e.g., DT-diaphorase (DTD) or biphenyl-hydrolase-like protein (BPHL)): 10. chemotherapeutic agent (for example, cisplatin) or any form of nanoparticle, etc.

Pharmaceutical Composition

The present invention also provides a composition. Preferably, the composition is a pharmaceutical composition, which comprises the above-mentioned antibody or its active fragment or its fusion protein, and a pharmaceutically acceptable carrier. Generally, these materials can be formulated in a non-toxic, inert and pharmaceutically acceptable aqueous carrier medium, wherein the pH is usually about 5-8, preferably about 6-8, although the pH value can be changed according to the nature of the substances formulated and the conditions to be treated. The prepared pharmaceutical composition can be administered by conventional routes, including (but not limited to): intratumoral, intraperitoneal, intravenous, or topical administration.

The pharmaceutical composition of the present invention can be directly used for binding PD-L1 and/or VEGF protein molecules, and thus can be used for treating a tumor. In addition, an additional therapeutic agent may also be used concomitantly.

The pharmaceutical composition of the present invention comprises a safe and effective amount (e.g., 0.001-99 wt %, preferably 0.01-90 wt %, more preferably 0.1-80 wt %) of the above-mentioned single-domain antibody (or its conjugate) of the present invention and a pharmaceutical acceptable carrier or excipient. Such carrier includes, but is not limited to: saline, buffer, dextrose, water, glycerol, ethanol, or a combination thereof. The pharmaceutical formulation should match the mode of administration. The pharmaceutical composition of the present invention can be prepared in the form of injection, for example, by conventional methods using physiological saline or aqueous solution containing glucose and other adjuvants. The pharmaceutical composition such as injection or solution is preferably produced under sterile conditions. The active ingredient is administered in a therapeutically effective amount, for example about 10 μg/kg body weight to about 50 mg/kg body weight per day. In addition, the polypeptide of the present invention can also be used with an additional therapeutic agent.

When using the pharmaceutical composition, a safe and effective amount of the immunoconjugate is administered to a mammal, wherein the safe and effective amount is usually at least about 10 μg/kg body weight, and in most cases no more than about 50 mg/kg body weight: preferably, the dosage is about 10 μg/kg body weight to about 10 mg/kg body weight. Nevertheless, factors such as the route of administration and the health status of the patient should also be considered for the specific dosage, which are within the skill of skilled physicians.

Labeled Antibody

In a preferred embodiment of the present invention, the antibody bears a detectable label. More preferably, the label is selected from a group consisting of isotope, colloidal gold label, colored label and fluorescent label.

Colloidal gold labeling can be performed using methods known to those skilled in the art. In a preferred embodiment of the present invention, the PD-L1/VEGF bispecific antibody can be labeled with a colloidal gold to obtain a colloidal gold-labeled antibody.

Detection Method

The present invention also relates to a method for detecting PD-L1 and/or VEGF proteins. The method roughly comprises the following steps: obtaining a sample of cell and/or tissue; dissolving the sample in a medium; detecting the level of PD-L1 and/or VEGF proteins in the dissolved sample.

In the detection method of the present invention, the sample used is not particularly limited, and a representative example is a cell-containing sample present in a cell preservation solution.

Kit

The present invention also provides a kit comprising the antibody (or its fragment) or detection plate of the present invention. In a preferred embodiment of the present invention, the kit further comprises a container, an instruction for use, a buffer, etc.

The present invention also provides a detection kit for detecting the level of PD-L1 and/or VEGF, and the kit comprises an antibody for recognizing PD-L1 and/or VEGF protein, a lysis medium for dissolving sample, and common detection reagents and buffers such as various buffers, detection labels, detection substrates, etc. The detection kit may be an in vitro diagnostic device.

Use

Experimental results show that the bispecific antibody of the present invention can target human PD-L1 protein with high specificity, can inhibit PD-1/PD-L1 pathway on the basis of targeting neutralizing VEGF in the tumor microenvironment, can restore the activity of T cells and enhance immune response, and thus more effectively improve the effect of inhibiting tumor occurrence and development.

As mentioned above, the single-domain antibody of the present invention has a wide range of biological and clinical application values, and its use involves many fields such as diagnosis and treatment of diseases related to PD-L1 and/or VEGF, basic medical research, biological research, etc. A preferred use is a use for clinical diagnosis and targeted therapy against PD-L1 and/or VEGF, such as tumor therapy.

Beneficial Effects of the Present Invention

The present invention achieves one or more of the following technical effects:
(1) The bispecific antibody of the present invention has a strong affinity.
(2) It is capable of inhibiting the PD-1/PD-L1 pathway on the basis of targeting and neutralizing VEGF in the tumor microenvironment, restoring the activity of T cells, enhancing the immune response, more effectively improving the effect of inhibiting tumor occurrence and development, and shows a good potential in the preparation of an anticancer drug.
(3) The production of the bispecific antibody of the present invention is simple and convenient.
(4) The bispecific antibody of the present invention likely shows a synergistic effect between the first protein functional region and the second protein functional region, for example, its affinity with VEGF is often better than that of anti-VEGF monoclonal antibody, and its affinity with PD-L1 is often better than that of anti-PD-L1 monoclonal antibody: it is also better than anti-VEGF monoclonal antibody or anti-PD-L1 monoclonal antibody in inducing mixed lymphocytes to secrete IL2 or INF, showing that the bispecific antibody of the present invention can better activate T cells.

Figures 1A, 1B:
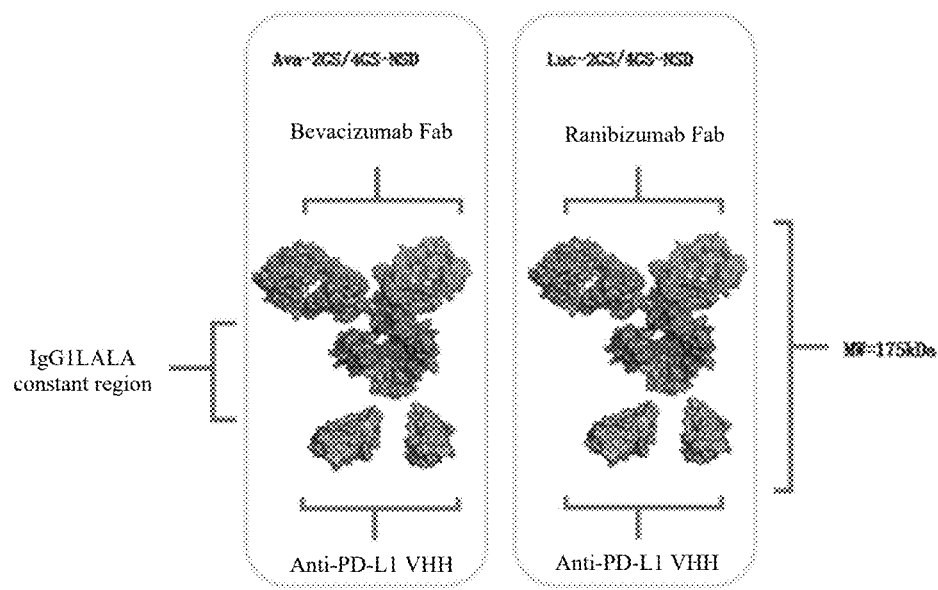
FIG. 1A shows a schematic diagram of the structure of Ava-2GS-NSD or Ava-4GS-NSD.
FIG. 1B shows a schematic structure of Luc-2GS-NSD or Luc-4GS-NSD.

Some sequences involved in the present invention are shown in Table B below.

TABLE B

| Name | Sequence | SEQ ID NO: |
|---|---|---|
| ava-2GS-NSD HC | EVQLVESGGGLVQPGGSLRLSCAASGYTFTNYGMNWVRQA PGKGLEWVGWINTYTGEPTY AADFKRRFTFSLDTSKSTAYL QMNSLRAEDTAVYYCAKYPHYYGSSHWYFDVWGQGTLVT VSSASTKGPSVFPLAPSSKSTSGGTAALGCLVKDYFPEPVTV SWNSGALTSGVHTFPAVLQSSGLYSLSSVVTVPSSSLGTQTY ICNVNHKPSNTKVDKKVEPKSCDKTHTCPPCPAPEAAGGPS VFLFPPKPKDTLMISRTPEVTCVVVDVSHEDPEVKFNWYVD GVEVHNAKTKPREEQYNSTYRVVSVLTVLHQDWLNGKEYK CKVSNKALPAPIEKTISKAKGQPREPQVYTLPPSRDELTKNQ VSLTCLVKGFYPSDIAVEWESNGQPENNYKTTPPVLDSDGSF | 1 |

TABLE B-continued

| Name | Sequence | SEQ ID NO: |
|---|---|---|
| | FLYSKLTVDKSRWQQGNVFSCSVMHEALHNHYTQKSLSLSP GGGGGSGGGGSGEVQLQESGGGLVQPGGSLRLSCAASGFTF SSYWMYWLRQAPGKGLEWVSSINSDSSTYYRDSVKGRFTI SRDNAKNTLYLQMNSLKSEDTAVYYCAKDPGGYAKGQGT QVTVSS | |
| ava-4GS-NSD HC | EVQLVESGGGLVQPGGSLRLSCAASGYTFTNYGMNWVRQA PGKGLEWVGWINTYTGEPTYAADFKRRFTFSLDTSKSTAYL QMNSLRAEDTAVYYCAKYPHYYGSSHWYFDVWGQGTLVT VSSASTKGPSVFPLAPSSKSTSGGTAALGCLVKDYFPEPVTV SWNSGALTSGVHTFPAVLQSSGLYSLSSVVTVPSSSLGTQTY ICNVNHKPSNTKVDKKVEPKSCDKTHTCPPCPAPEAAGGPS VFLFPPKPKDTLMISRTPEVTCVVVDVSHEDPEVKFNWYVD GVEVHNAKTKPREEQYNSTYRVVSVLTVLHQDWLNGKEYK CKVSNKALPAPIEKTISKAKGQPREPQVYTLPPSRDELTKNQ VSLTCLVKGFYPSDIAVEWESNGQPENNYKTTPPVLDSDGSF FLYSKLTVDKSRWQQGNVFSCSVMHEALHNHYTQKSLSLSP GGGGSGGGGSGGGGSGGGGSGEVQLQESGGGLVQPGGSL RLSCAASGFTFSSYWMYWLRQAPGKGLEWVSSINSDSSTY YRDSVKGRFTISRDNAKNTLYLQMNSLKSEDTAVYYCAKD PGGYAKGQGTQVTVSS | 2 |
| Bevacizumab VH | EVQLVESGGGLVQPGGSLRLSCAASGYTFTNYGMNWVRQA PGKGLEWVGWINTYTGEPTYAADFKRRFTFSLDTSKSTAYL QMNSLRAEDTAVYYCAKYPHYYGSSHWYFDVWGQGTLVT VSS | 3 |
| IgG1 CH(LALA) | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDKTHTCPPCPAPEAAGGPSVFL FPPKPKDTLMISRTPEVTCVVVDVSHEDPEVKFNWYVDGVE VHNAKTKPREEQYNSTYRVVSVLTVLHQDWLNGKEYKCK VSNKALPAPIEKTISKAKGQPREPQVYTLPPSRDELTKNQVS LTCLVKGFYPSDIAVEWESNGQPENNYKTTPPVLDSDGSFFL YSKLTVDKSRWQQGNVFSCSVMHEALHNHYTQKSLSLSPG | 4 |
| C-Ye-18-5 | EVQLQESGGGLVQPGGSLRLSCAASGFTFSSYWMYWLRQA PGKGLEWVSSINSDSSTYYRDSVKGRFTISRDNAKNTLYLQ MNSLKSEDTAVYYCAKDPGGYAKGQGTQVTVSS | 5 |
| G4S2 | GGGGSGGGGSG | 6 |
| G4S4 | GGGGSGGGGSGGGGSGGGGSG | 7 |
| ava-LC | DIQMTQSPSSLSASVGDRVTITCSASQDISNYLNWYQQKPGK APKVLIYFTSSLHSGVPSRFSGSGSGTDFTLTISSLQPEDFATY YCQQYSTVPWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 8 |
| Bevacizumab VL | DIQMTQSPSSLSASVGDRVTITCSASQDISNYLNWYQQKPGK APKVLIYFTSSLHSGVPSRFSGSGSGTDFTLTISSLQPEDFATY YCQQYSTVPWTFGQGTKVEIK | 9 |
| Human κ light chain | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC | 10 |
| Luc-2GS-NSD HC | EVQLVESGGGLVQPGGSLRLSCAASGYDFTHYGMNWVRQA PGKGLEWVGWINTYTGEPTY AADFKRRFTFSLDTSKSTAYL QMNSLRAEDTAVYYCAKYPYYYGTSHWYFDVWGQGTLVT VSSASTKGPSVFPLAPSSKSTSGGTAALGCLVKDYFPEPVTV SWNSGALTSGVHTFPAVLQSSGLYSLSSVVTVPSSSLGTQTY ICNVNHKPSNTKVDKKVEPKSCDKTHTCPPCPAPEAAGGPS VFLFPPKPKDTLMISRTPEVTCVVVDVSHEDPEVKFNWYVD GVEVHNAKTKPREEQYNSTYRVVSVLTVLHQDWLNGKEYK CKVSNKALPAPIEKTISKAKGQPREPQVYTLPPSRDELTKNQ VSLTCLVKGFYPSDIAVEWESNGQPENNYKTTPPVLDSDGSF FLYSKLTVDKSRWQQGNVFSCSVMHEALHNHYTQKSLSLSP GGGGGSGGGGSGEVQLQESGGGLVQPGGSLRLSCAASGFTF SSYWMYWLRQAPGKGLEWVSSINSDSSTYYRDSVKGRFTI SRDNAKNTLYLQMNSLKSEDTAVYYCAKDPGGYAKGQGT QVTVSS | 11 |

TABLE B-continued

| Name | Sequence | SEQ ID NO: |
|---|---|---|
| Luc-4GS-NSD HC | EVQLVESGGGLVQPGGSLRLSCAASGYDFTHYGMNWVRQA PGKGLEWVGWINTYTGEPTYAADFKRRFTFSLDTSKSTAYL QMNSLRAEDTAVYYCAKYPYYYGTSHWYFDVWGQGTLVT VSSASTKGPSVFPLAPSSKSTSGGTAALGCLVKDYFPEPVTV SWNSGALTSGVHTFPAVLQSSGLYSLSSVVTVPSSSLGTQTY ICNVNHKPSNTKVDKKVEPKSCDKTHTCPPCPAPEAAGGPS VFLFPPKPKDTLMISRTPEVTCVVVDVSHEDPEVKFNWYVD GVEVHNAKTKPREEQYNSTYRVVSVLTVLHQDWLNGKEYK CKVSNKALPAPIEKTISKAKGQPREPQVYTLPPSRDELTKNQ VSLTCLVKGFYPSDIAVEWESNGQPENNYKTTPPVLDSDGSF FLYSKLTVDKSRWQQGNVFSCSVMHEALHNHYTQKSLSLSP GGGGGSGGGGSGGGGSGGGGSGEVQLQESGGGLVQPGGSL RLSCAASGFTFSSYWMYWLRQAPGKGLEWVSSINSDSSSTY YRDSVKGRFTISRDNAKNTLYLQMNSLKSEDTAVYYCAKD PGGYAKGQGTQVTVSS | 12 |
| Luc VH | EVQLVESGGGLVQPGGSLRLSCAASGYDFTHYGMNWVRQA PGKGLEWVGWINTYTGEPTYAADFKRRFTFSLDTSKSTAYL QMNSLRAEDTAVYYCAKYPYYYGTSHWYFDVWGQGTLVT VSS | 13 |
| Luc-LC | DIQLTQSPSSLSASVGDRVTITCSASQDISNYLNWYQQKPGK APKVLIYFTSSLHSGVPSRFSGSGSGTDFTLTISSLQPEDFATY YCQQYSTVPWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 14 |
| Luc VL | DIQLTQSPSSLSASVGDRVTITCSASQDISNYLNWYQQKPGK APKVLIYFTSSLHSGVPSRFSGSGSGTDFTLTISSLQPEDFATY YCQQYSTVPWTFGQGTKVEIK | 15 |
| NSD-Elyea | EVQLQESGGGLVQPGGSLRLSCAASGFTFSSYWMYWLRQA PGKGLEWVSSINSDSSSTYYRDSVKGRFTISRDNAKNTLYLQ MNSLKSEDTAVYYCAKDPGGYAKGQGTQVTVSSDKTHTCP PCPAPEAAGGPSVFLFPPKPKDTLMISRTPEVTCVVVDVSHE DPEVKFNWYVDGVEVHNAKTKPREEQYNSTYRVVSVLTVL HQDWLNGKEYKCKVSNKALPAPIEKTISKAKGQPREPQVYT LPPSRDELTKNQVSLTCLVKGFYPSDIAVEWESNGQPENNY KTTPPVLDSDGSFFLYSKLTVDKSRWQQGNVFSCSVMHEAL HNHYTQKSLSLSPGGGGGSGGGGSGGGGSGGGGSGSDTGR PFVEMYSEIPEIIHMTEGRELVIPCRVTSPNITVTLKKFPLDTL IPDGKRIIWDSRKGFIISNATYKEIGLLTCEATVNGHLYKTNY LTHRQTNTIIDVVLSPSHGIELSVGEKLVLNCTARTELNVGID FNWEYPSSKHQHKKLVNRDLKTQSGSEMKKFLSTLTIDGVT RSDQGLYTCAASSGLMTKKNSTFVRVHEK | 16 |
| Elyea | SDTGRPFVEMYSEIPEIIHMTEGRELVIPCRVTSPNITVTLKKF PLDTLIPDGKRIIWDSRKGFIISNATYKEIGLLTCEATVNGHL YKTNYLTHRQTNTIIDVVLSPSHGIELSVGEKLVLNCTARTE LNVGIDFNWEYPSSKHQHKKLVNRDLKTQSGSEMKKFLSTL TIDGVTRSDQGLYTCAASSGLMTKKNSTFVRVHEK | 17 |
| Fc(LALA) | DKTHTCPPCPAPEAAGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGNVFSCS VMHEALHNHYTQKSLSLSPG | 18 |
| Elyea-NSD | SDTGRPFVEMYSEIPEIIHMTEGRELVIPCRVTSPNITVTLKKF PLDTLIPDGKRIIWDSRKGFIISNATYKEIGLLTCEATVNGHL YKTNYLTHRQTNTIIDVVLSPSHGIELSVGEKLVLNCTARTE LNVGIDFNWEYPSSKHQHKKLVNRDLKTQSGSEMKKFLSTL TIDGVTRSDQGLYTCAASSGLMTKKNSTFVRVHEKDKTHTC PPCPAPEAAGGPSVFLFPPKPKDTLMISRTPEVTCVVVDVSH EDPEVKFNWYVDGVEVHNAKTKPREEQYNSTYRVVSVLTV LHQDWLNGKEYKCKVSNKALPAPIEKTISKAKGQPREPQVY TLPPSRDELTKNQVSLTCLVKGFYPSDIAVEWESNGQPENNY KTTPPVLDSDGSFFLYSKLTVDKSRWQQGNVFSCSVMHEAL HNHYTQKSLSLSPGGGGGSGGGGSGGGGSGGGGSGEVQLQ ESGGGLVQPGGSLRLSCAASGFTFSSYWMYWLRQAPGKGL EWVSSINSDSSSTYYRDSVKGRFTISRDNAKNTLYLQMNSLK SEDTAVYYCAKDPGGYAKGQGTQVTVSS | 19 |

TABLE B-continued

| Name | Sequence | SEQ ID NO: |
|---|---|---|
| CH1 | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDKTHT | 20 |
| Bevacizumab HCDR1 | GYTFTNYG | 21 |
| Bevacizumab HCDR2 | INTYTGEPT | 22 |
| Bevacizumab HCDR3 | AKYPHYYGSSHWYFDV | 23 |
| Bevacizumab LCDR1 | QDISNY | 24 |
| Bevacizumab LCDR2 | FTS | 25 |
| Bevacizumab LCDR3 | QQYSTVPWT | 26 |
| Ranibizumab HCDR1 | GYDFTHYG | 27 |
| Ranibizumab HCDR2 | Same as Bevacizumab HCDR2 | 22 |
| Ranibizumab HCDR3 | AKYPYYYGTSHWYFDV | 28 |
| Ranibizumab LCDR1 | Same as Bevacizumab LCDR1 | 24 |
| Ranibizumab LCDR2 | Same as Bevacizumab LCDR2 | 25 |
| Ranibizumab LCDR3 | Same as Bevacizumab LCDR3 | 26 |
| C-Ye-18-5 heavy chain variable region HCDR1 | GFTFSSYW | 29 |
| C-Ye-18-5 heavy chain variable region HCDR2 | INSDSSST | 30 |
| C-Ye-18-5 heavy chain variable region HCDR3 | AKDPGGYA | 31 |

Specific Models for Carrying Out the Present Invention

The present invention is further illustrated in conjunction with specific examples. It should be understood that these examples are only used to illustrate the present invention and are not intended to limit the scope of the present invention. The experimental methods without giving specific conditions in the following examples are usually carried out according to conventional conditions, such as the conditions described in Sambrook et al., Molecular cloning: Laboratory Manual (New York: Cold Spring Harbor Laboratory Press, 1989), or according to the conditions recommended by the manufacturer. Percentages and parts are by weight unless otherwise indicated.

Figure 7A:
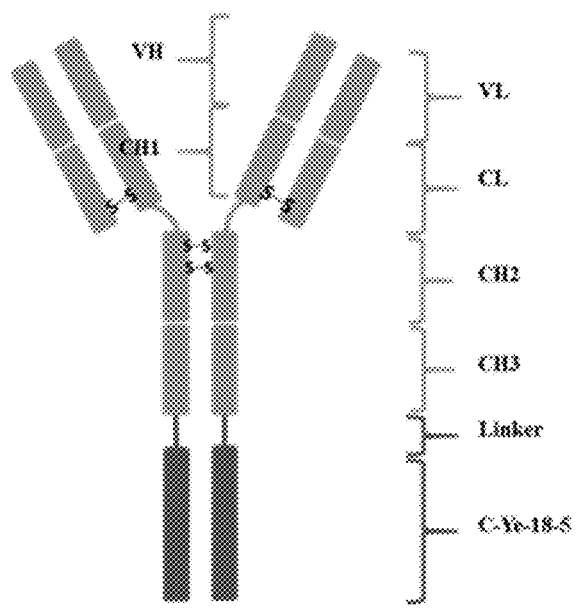
FIG. 7A shows a schematic diagram of the structure of Ava-2GS-NSD or Ava-4GS-NSD.

Example 1: Cloning and Expression of Anti-VEGF/PD-L1 Bispecific Antibody 1.1 Antibody Structure Design In this example, 6 anti-VEGF/PD-L1 bispecific antibodies were constructed, namely:
Ava-2GS-NSD/Ava-4GS-NSD: It composed of 4 polypeptide chains (2 heavy chains ligated to C-Ye-18-5 respectively, and 2 light chains), schematic diagram of which were shown in FIG. 1A and FIG. 7A, in which both peptide chains #1 had the amino acid sequence set forth in SEQ ID NO: 1 or SEQ ID NO: 2, which contained the VH amino acid sequence (SEQ ID NO: 3) derived from the anti-VEGF antibody Bevacizumab (Patent No.: WO1998045332), the C-terminal of the VH amino acid sequence was directly ligated to the CH amino acid sequence derived from human IgG1 (LALA mutation was introduced to reduce the Fc function, SEQ ID NO: 4), and the N-terminal of the anti-PD-L1 nanobody C-Ye-18-5 (patent application number: 2019108631090) (SEQ ID NO: 5) was ligated to the C-terminal of the heavy chain through a flexible peptide of 11 amino acid residues (G4S) 2G (SEQ ID NO: 6) (Ava-2GS-NSD) or 21 amino acid residues (G+S)+G (SEQ ID NO: 7) (Ava-4GS-NSD). Both peptide chains #2 had the amino acid sequence set forth in SEQ ID NO: 8, which contained the VL amino acid sequence (SEQ ID NO: 9) derived from the anti-VEGF antibody Bevacizumab, and the human κ light chain constant region (CL) amino acid sequence (SEQ ID NO: 10) ligated to the C-terminal of the VL amino acid sequence.

Figure 7B:
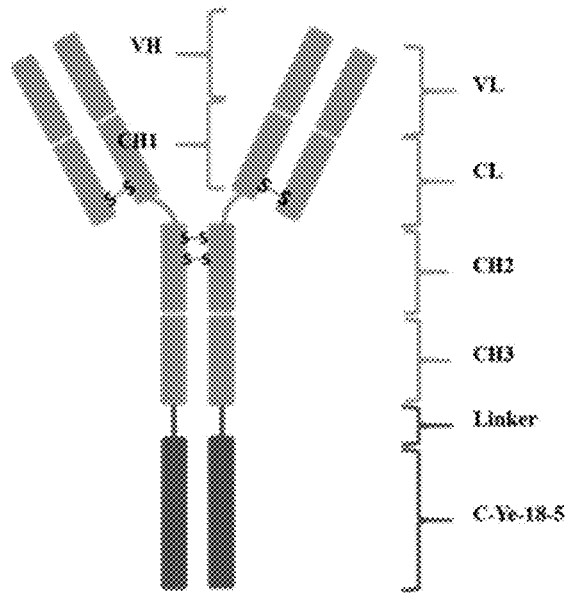
FIG. 7B shows a schematic diagram of the structure of Luc-2GS-NSD or Luc-4GS-NSD.

Luc-2GS-NSD/Luc-4GS-NSD: It composed of 4 polypeptide chains (2 heavy chains ligated to C-Ye-18-5 respectively, and 2 light chains), the schematic diagrams of which were shown in FIG. 1B and FIG. 7B, in which both peptide chains #1 had the amino acid sequence set forth in SEQ ID NO: 11 or SEQ ID NO: 12, which contained the VH amino acid sequence (SEQ ID NO: 13) derived from the anti-VEGF antibody Ranibizumab (Patent No.: WO2018175752), the C-terminal of the VH amino acid sequence was directly ligated to the CH amino acid sequence derived from human IgG1 (LALA mutation was introduced to reduce the Fc function, SEQ ID NO: 4), and the N-terminal of the anti-PD-L1 nanobody C-Ye-18-5 (SEQ ID NO: 5) was ligated to the C-terminal of the heavy chain through a flexible peptide of 11 amino acid residues $(G_4S)_2G$ (SEQ ID NO: 6) (Luc-2GS-NSD) or 21 amino acid residues $(G_4S)_4G$ (SEQ ID NO: 7) (Luc-4GS-NSD). Both peptide chains #2 had the amino acid sequence set forth in SEQ ID NO: 14, which contained the VL amino acid sequence (SEQ ID NO: 15) derived from the anti-VEGF antibody Ranibizumab, and the human κ light chain constant region (CL) (SEQ ID NO: 10) ligated to the C-terminal of the VL amino acid sequence.

Figures 1C, 1D:
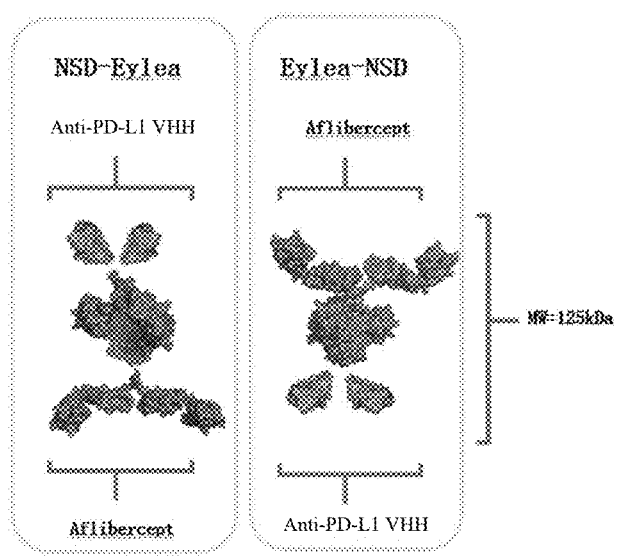
FIG. 1C shows a schematic diagram of the structure of NSD-Elyea.
FIG. 1D shows a schematic diagram of the structure of Elyea-NSD.
Figure 7C:
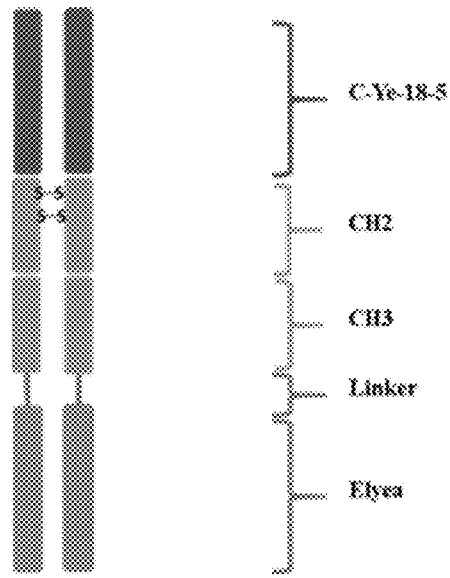
FIG. 7C shows a schematic diagram of the structure of NSD-Elyea.

NSD-Elyea: It composed of 2 identical polypeptide chains (dimer), the schematic diagrams of which were shown in FIG. 1C and FIG. 7C, in which the peptide chains had the amino acid sequence set forth in SEQ ID NO: 16, which contained the VEGF binding region (Elyea. SEQ ID NO: 17) derived from the anti-VEGF fusion protein Aflibercept (patent number: U.S. Pat. No. 7,070,959), the C-terminal of the amino acid sequence was directly ligated to the Fc amino acid sequence derived from human IgG1 (LALA mutation was introduced to reduce the Fc function, SEQ ID NO: 18), and the N-terminal of the anti-PD-L1 nanobody C-Ye-18-5 was ligated to the C-terminal of the heavy chain through a flexible peptide of 21 amino acid residues $(G_4S)_4G$ (SEQ ID NO: 7).

Figure 7D:
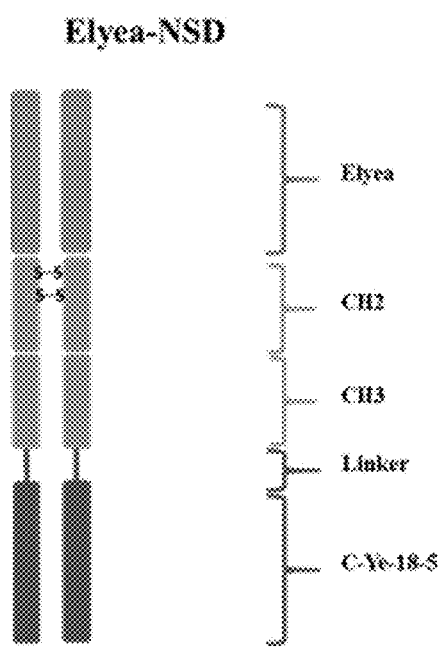
FIG. 7D shows a schematic diagram of the structure of Elyea-NSD.

Elyea-NSD: It composed of 2 identical polypeptide chains (dimer), the structural schematic diagram of which were shown in FIG. 1D and FIG. 7D, in which the peptide chains had the amino acid sequence set forth in SEQ ID NO: 19, which contained the anti-PD-L1 nanobody C-Ye-18-5 (SEQ ID NO: 5), the C-terminal of the nanobody sequence was directly ligated to the Fc amino acid sequence derived from human IgG1 (LALA mutation was introduced to reduce the Fc function, SEQ ID NO: 18), and the N-terminal of the VEGF-binding region (Elyea, SEQ ID NO: 17) derived from the anti-VEGF fusion protein Aflibercept was ligated to the C-terminal of the heavy chain through a flexible peptide of 21 amino acid residues $(G_4S)_4G$ (SEQ ID NO: 7).

1.2 Gene Cloning and Protein Preparation

Referring to the sequences in Table B, the gene fragments encoding the corresponding amino acid sequences were constructed into the pCDNA3.1 vector. For the peptide chain #1 and peptide chain #2 in Ava-2GS-NSD, these two sequences were expressed in two different plasmids during transient transfection, and disulfide would be automatically formed during the cell expression procedure.

ExpiCHO™ Expression System Kit (purchased from Thermo) was used to transfect the plasmids into Expi-CHO cells, and the transfection method was carried out according to the manufacturer's instructions. After the cells were cultured for 5 days, the supernatant was collected and subjected to sorting method using protein A magnetic beads (purchased from GenScript) to purify the target protein. The magnetic beads were resuspended with an appropriate volume of binding buffer (PBS+0.1% Tween 20, pH 7.4) (1-4 times the volume of magnetic beads) and then added to the sample to be purified, incubated at room temperature for 1 hour with gentle shaking. The sample was placed on a magnetic stand (purchased from Beaver), the supernatant was discarded, and the magnetic beads were washed 3 times with binding buffer. Elution buffer (0.1M sodium citrate, pH 3.2) was added according to 3-5 times the volume of the magnetic beads, shaken at room temperature for 5-10 min, placed on the magnetic stand, the elution buffer was collected, transferred a collection tube into which neutralization buffer (1M Tris, pH8.54) had been added, and mixed well. It was used in next experiments.

Example 2: Determination of Antibody Affinity of Bispecific Antibody

ForteBio affinity determination was performed according to the existing method (Estep, P et al., Solution-based measurement of high-throughput antibody-antigen affinity and epitope fractionation, MAbs, 2013.5 (2): p. 270-8). Briefly, the sensor was equilibrated offline for 30 min in assay buffer, then measured online for 60 s to establish a baseline, and the purified antibody obtained as described above was loaded onto the AHC sensor online. Then the sensor was placed in 100 nM PD-L1 or VEGF antigen for 5 minutes, and then the sensor was transferred to PBS for dissociation for 5 minutes. The analysis of kinetics was performed using a 1:1 binding model.

The results were shown in Table 1 and Table 2 below.

TABLE 1

| Binding affinity of candidate molecules to PD-L1 | | | |
| --- | --- | --- | --- |
| No. | $K_D$(M) | Kon(1/Ms) | Koff(1/s) |
| Ava-2GS-NSD | 8.48E−09 | 3.19E+05 | 2.70E−03 |
| Luc-2GS-NSD | 9.52E−09 | 2.81E+05 | 2.67E−03 |
| Ava-4GS-NSD | 7.12E−09 | 3.54E+05 | 2.52E−03 |
| Luc-4GS-NSD | 8.08E−09 | 3.21E+05 | 2.60E−03 |
| NSD-Elyea | 5.33E−09 | 3.22E+05 | 1.72E−03 |
| Elyea-NSD | 8.34E−09 | 3.39E+05 | 2.83E−03 |
| C-Ye-18-5 | 8.75E−09 | 1.98E+05 | 1.73E−03 |

TABLE 2

Binding affinity of candidate molecules to VEGF

| No. | $K_D$(M) | Kon(1/Ms) | Koff(1/s) |
| --- | --- | --- | --- |
| Ava-2GS-NSD | 1.38E−09 | 2.59E+05 | 3.58E−04 |
| Luc-2GS-NSD | 1.33E−09 | 1.77E+05 | 2.36E−04 |
| Ava-4GS-NSD | 1.51E−09 | 2.49E+05 | 3.75E−04 |
| Luc-4GS-NSD | 1.35E−09 | 1.82E+05 | 2.45E−04 |
| NSD-Elyea | 1.10E−09 | 6.48E+05 | 7.12E−04 |
| Elyea-NSD | 4.01E−10 | 9.14E+05 | 3.66E−04 |
| Ranibizumab | 2.29E−09 | 1.75E+05 | 4.00E−04 |
| Bevacizumab | 1.79E−09 | 1.71E+05 | 3.06E−04 |

The results showed that all the bispecific antibody samples of the present invention had binding activity to PD-L1 and VEGF proteins. Compared with the control antibody C-Ye-18-5 (PD-L1 single-domain antibody), the binding activity of the bispecific antibodies of the present invention to PD-L1 was similar or even better; and/or, compared with the control antibodies Ranibizumab and Bevacizumab, the binding activity of the bispecific antibodies of the present invention to VEGF was comparable or even better.

Example 3: Binding of Purified Bispecific Antibodies to PD-L1

The CHO cell line overexpressing human PD-L1 (CHO-hPD-L1 cells) was generated by transfecting pCHO1.0 vector (purchased from Invitrogen) with human PD-L1 cDNA (purchased from Sino Biological) cloned into MCS. The expanded CHO-hPD-L1 cells was adjusted to a cell density of 2×106 cells/ml, added to a 96-well flow plate, 100 μl/well, and centrifuged for later use. The purified PD-L1 antibody was diluted with PBS by 3-fold dilution starting from 400 nM to obtain a total of 12 points. The above-mentioned diluted sample was added into the above-mentioned cells-bearing 96-well flow plate, 100 μl/well, incubated at 4° C. for 30 min, and washed with PBS twice. Goat F(ab') 2 anti-human IgG-Fc (PE) (purchased from Abcam) diluted 100 times with PBS was added, 100 μl/well, incubated at 4° C. for 30 min, and washed twice with PBS. PBS was added, 100 μl/well, to resuspend the cells, and CytoFlex (Bechman) flow cytometer was used for detection and calculating the corresponding MFI.

Figure 2:
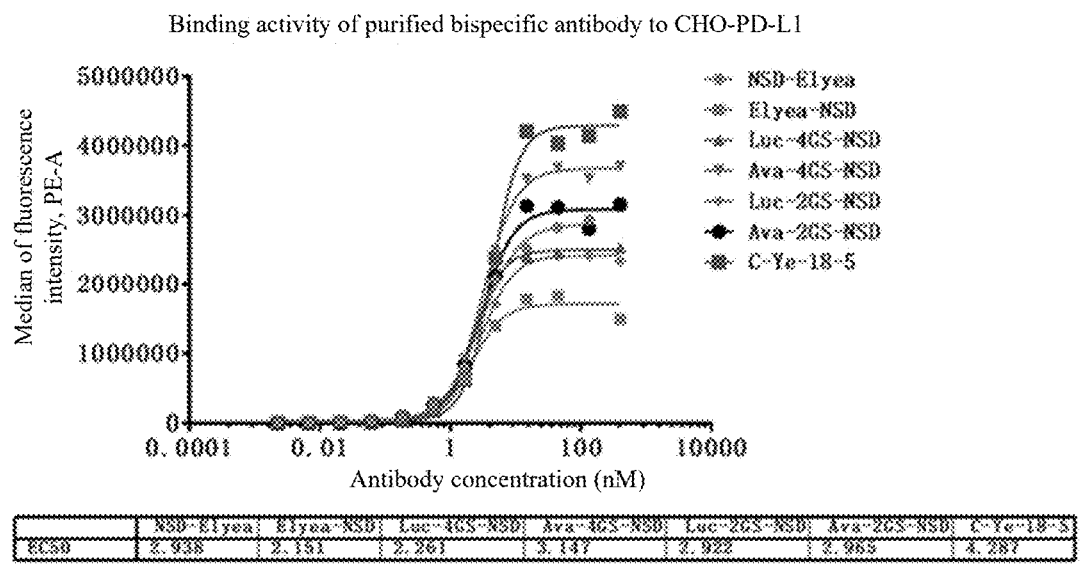
FIG. 2 shows a binding curve of the bispecific antibody to CHO-PDL1 cells.

The results were shown in FIG. 2. All the purified samples of the present invention had binding activity to CHO-hPD-L1 cells, and the binding activity of the purified samples was comparable to or even better than that of the control antibody C-Ye-18-5.

Example 4: ELISA Based Detection of VEGF/VEGFR Blocking Activity

Human VEGFR protein was diluted to an appropriate concentration with ELISA coating solution, added to ELISA plate, and coated overnight at 4° C. Blocking was performed with 5% BSA for 1 hour at room temperature. The samples to be tested were serially diluted and co-incubated with biotin-labeled human VEGF protein for 1 hour at room temperature. The incubated samples were added to the sealed ELISA plate and reacted at room temperature for 2 hours. After washing with PBS washing solution for 3 times, the diluted streptavidin (HRP) was added and reacted at room temperature for 1 hour; after washing with PBS washing solution for 3 times, ELISA chromogenic solution was added, allowed to stand at room temperature for 3 minutes, ELISA stop solution was added, and absorbance value at 450 nm was read.

Figure 3A:
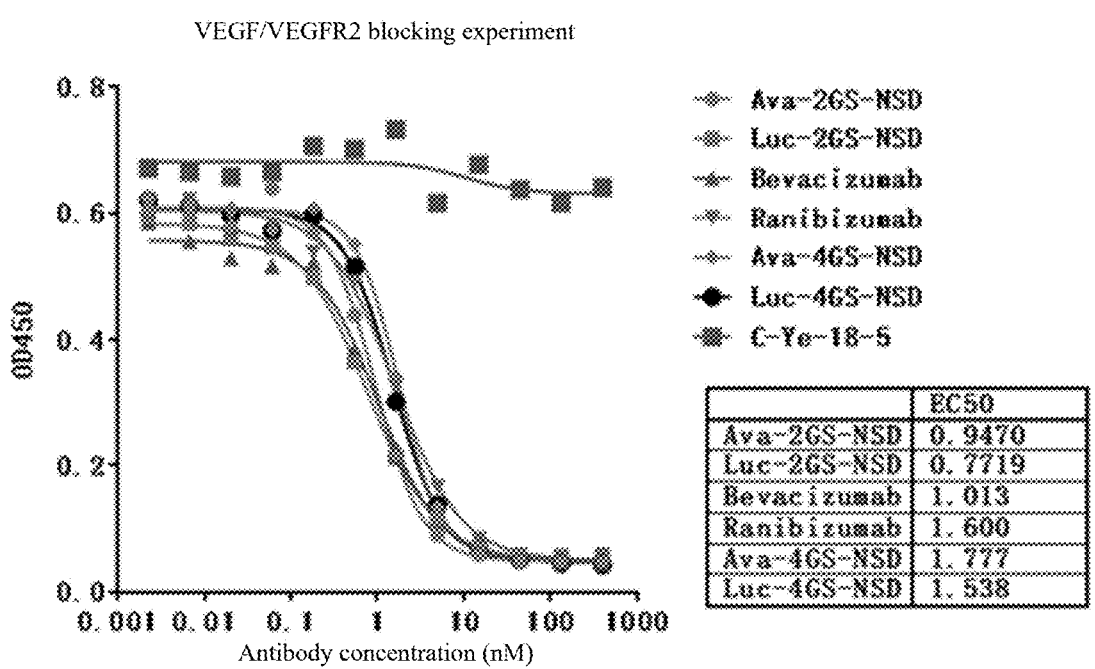
FIG. 3A shows a curve of the bispecific antibody blocking the binding of VEGF to VEGFR2.
Figure 3B:
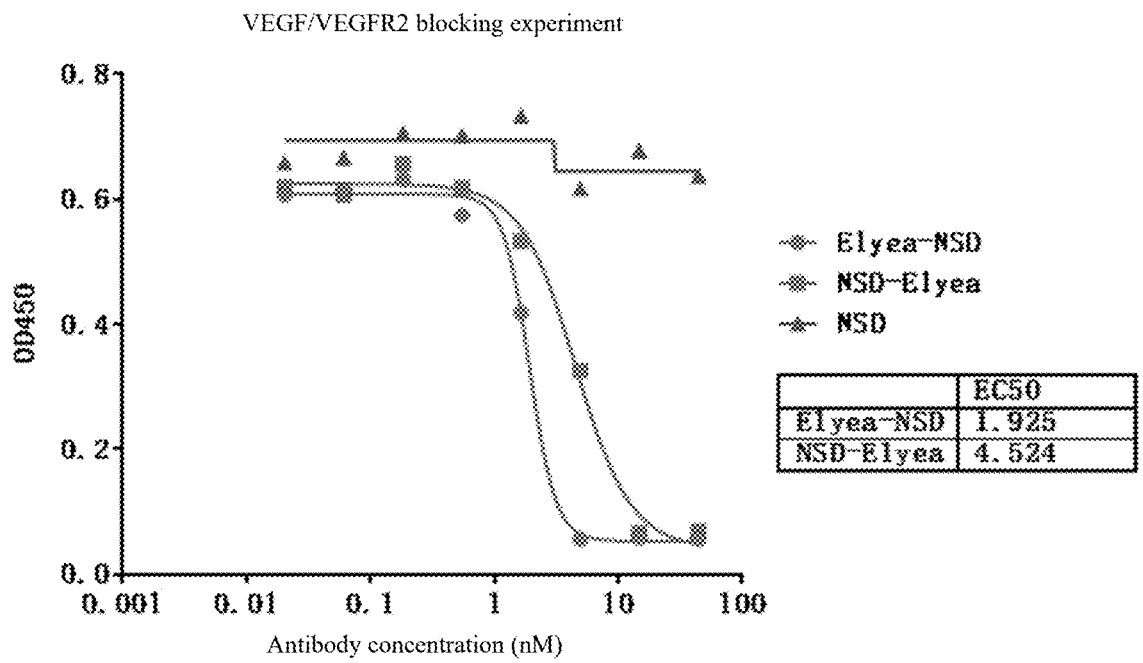
FIG. 3B shows a curve of the bispecific antibody blocking the binding of VEGF to VEGFR2.

The results were shown in FIG. 3A to FIG. 3B.

The results showed that Ava-2GS-NSD, Luc-2GS-NSD, Ava-4GS-NSD, Luc-4GS-NSD (FIG. 3A) and NSD-Elyea, Elyea-NSD (FIG. 3B) could completely block the interaction between VEGF and VEGFR protein.

Example 5: Mixed Lymphocyte Reaction Experiment

In this example, the activation of T cells by bispecific antibody samples was detected by mixed lymphocyte reaction experiment (MLR). The specific experimental method was as follows.

PBMC cells (purchased from SAILY BIO, SLB-HPB) were resuscitated, and centrifuged, the PBMC cells were resuspended with 10 ml of X-VIVO-15 medium (purchased from LONZA), cultured in a cell culture incubator at 37° C. for 2 hours, and the non-adherent cells were removed by pipetting. 10 ml of DC medium (X-VIVO-15 medium with 10 ng/ml GM-CSF (purchased from R&D), 20 ng/ml IL-4) was added, and cultured for 3 days. 5 ml of DC medium was supplemented, and the culturing was continued until the 6th day, DC maturation medium (X-VIVO-15 medium with 1000 U/ml TNF-α (purchased from R&D), 10 ng/ml IL-6 (purchased from R&D), 5 ng/ml IL-1 (purchased from R&D), 1 μM PGE2 (purchased from Tocris)) was added, and the culturing was performed for 2 days. The matured DC cells were harvested, and adjusted with X-VIVO-15 medium to a cell density of 2×10$^5$ cells/ml.

PBMC cells from another donor (purchased from SAILY BIO, SLB-HPB) were resuscitated and centrifuged. The PBMC cells were resuspended with 10 ml of X-VIVO-15 medium. CD4+ T cells were enriched with CD4+ T cell sorting kit (purchased from Stemcell), resuspended in X-VIVO-15, and the cell density was adjusted to 2×106 cells/ml. The CD4+ T cells were mixed with the matured DC cells collected above at a ratio of 1:1, and added to a 96-well U-bottom plate, 100 μl/well.

The purified bispecific antibody sample was diluted with X-VIVO-15 medium by 3-fold dilution starting from 200 nM to obtain a total of 9 points, and added to the above mixed cell well, 100 μl/well, and cultured for 5 days. The supernatant was collected, and detected by ELISA (purchased from eBioscience) method for the expression levels of IFN-γ (FIG. 4A) and IL2 (FIG. 4B).

Figure 4A:
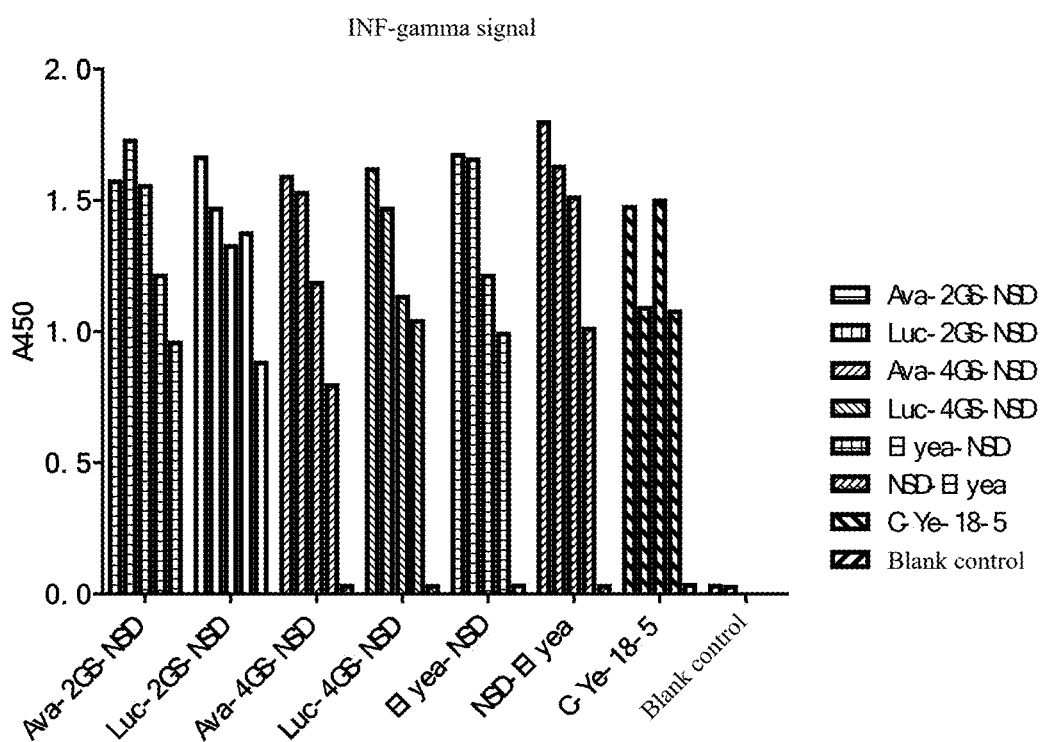
FIG. 4A shows the concentrations of the bispecific antibody for blocking the secretion of INF-gamma in a mixed lymphocyte culture. For each bispecific antibody sample, its concentrations from left to right are 100 nM, 10 nM, 1 nM, 0.1 nM and 0.01 nM.
Figure 4B:
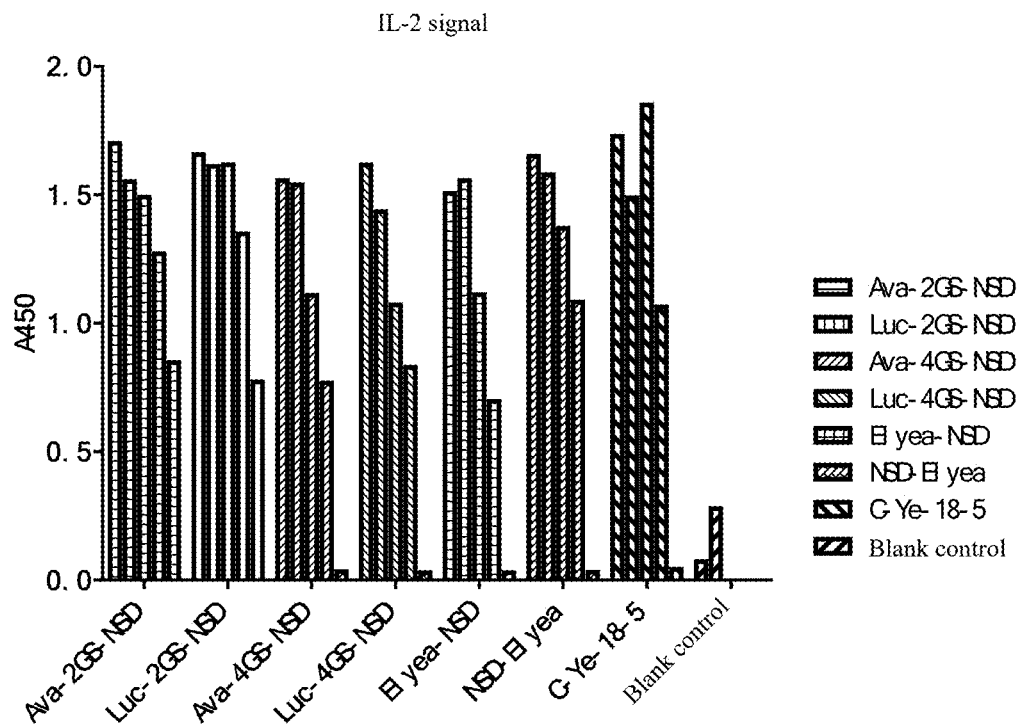
FIG. 4B shows the concentrations of the bispecific antibody for blocking the secretion of IL-2 in a mixed lymphocyte culture. For each bispecific antibody sample, its concentrations from left to right are 100 nM, 10 nM, 1 nM, 0.1 nM and 0.01 nM.
Figure 5A:
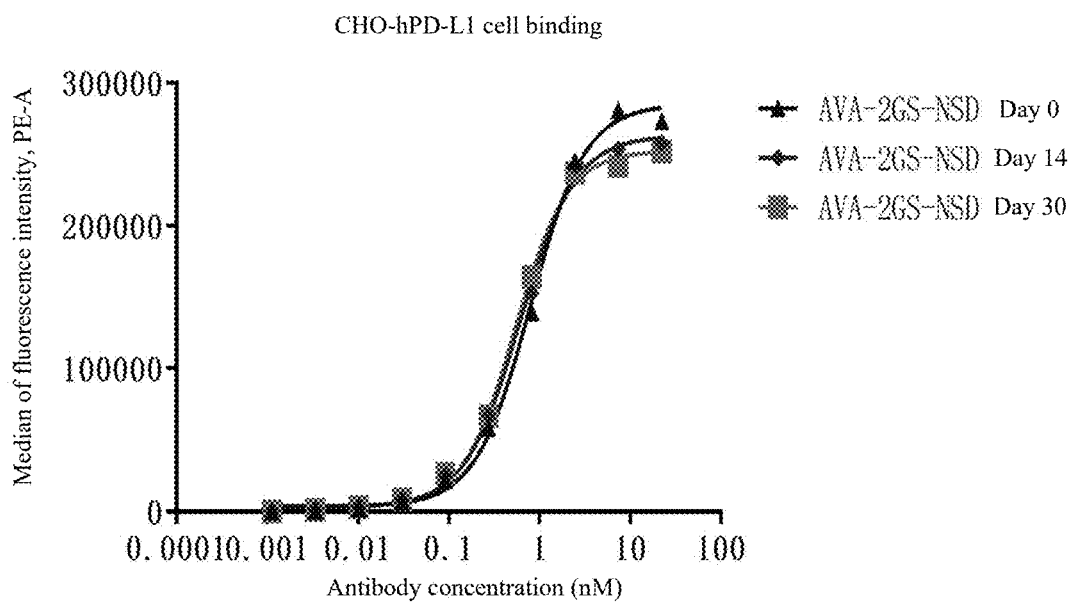
FIG. 5A shows the binding curves of the bispecific antibody stored for different days to CHO-PDL1 cells.
Figure 5B:
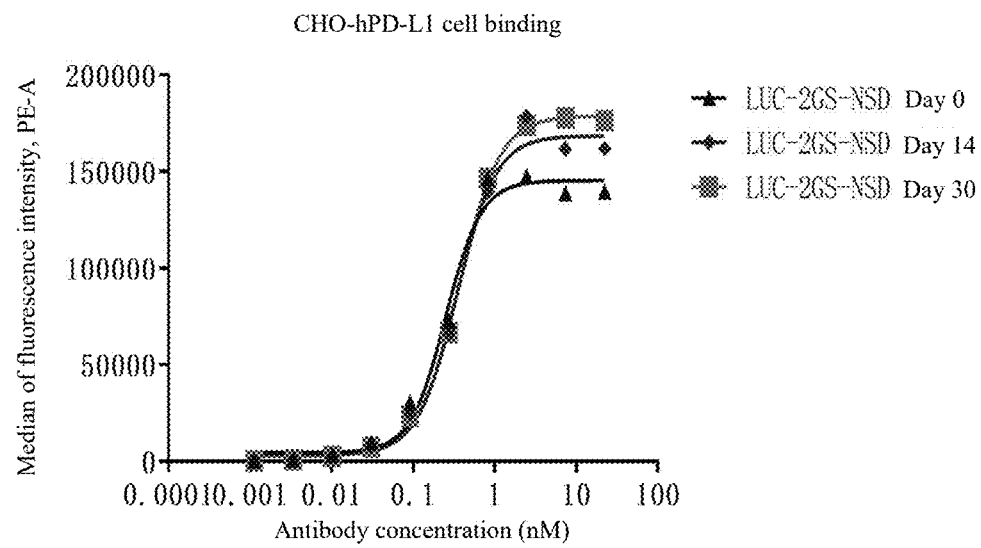
FIG. 5B shows the binding curves of the bispecific antibody stored for different days to CHO-PDL1 cells.
Figure 5C:
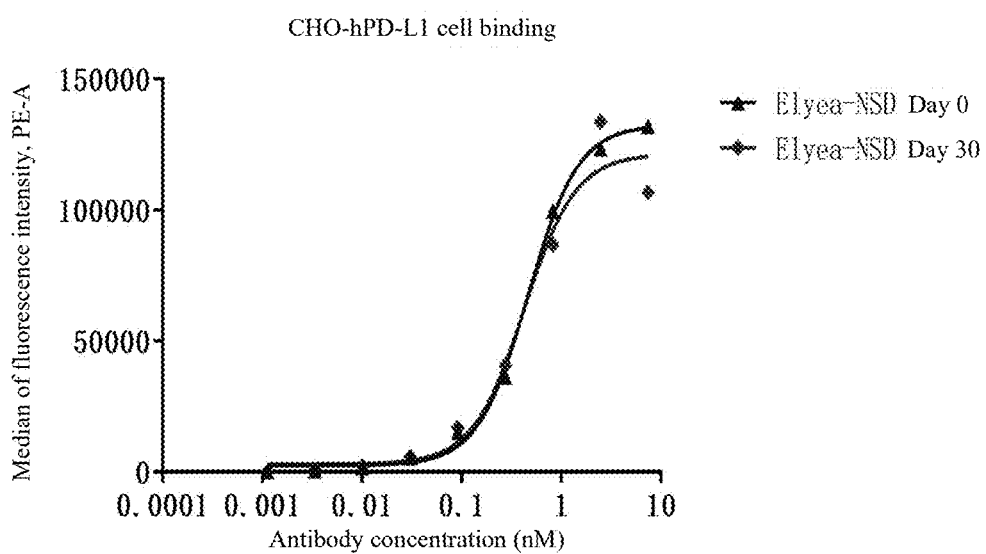
FIG. 5C shows the binding curves of the bispecific antibody stored for different days to CHO-PDL1 cells.
Figure 5D:
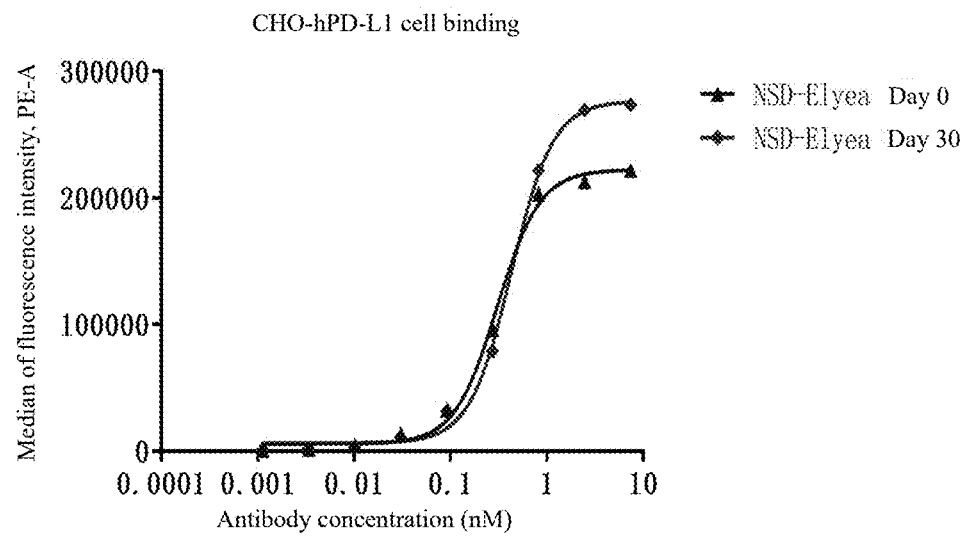
FIG. 5D shows the binding curves of the bispecific antibody stored for different days to CHO-PDL1 cells.
Figure 5E:
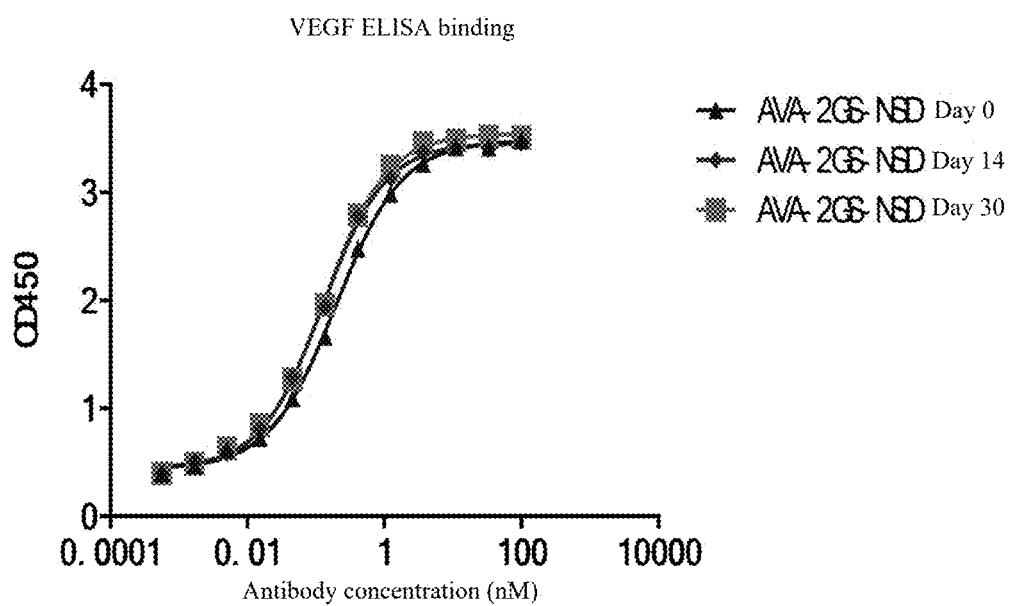
FIG. 5E shows the binding curves of the bispecific antibody stored for different days to VEGF.
Figure 5F:
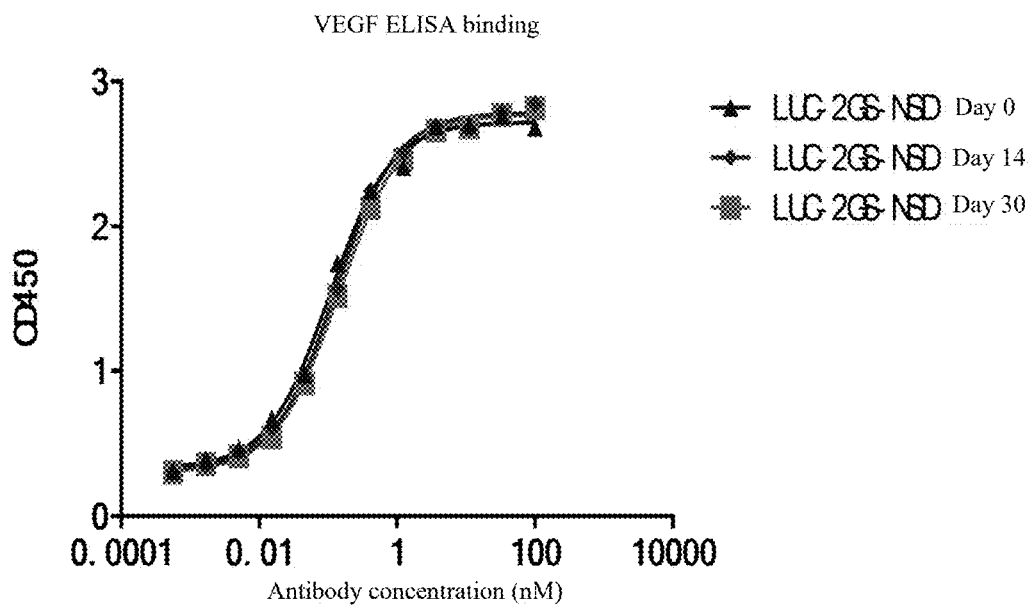
FIG. 5F shows the binding curves of the bispecific antibody stored for different days to VEGF.
Figure 5G:
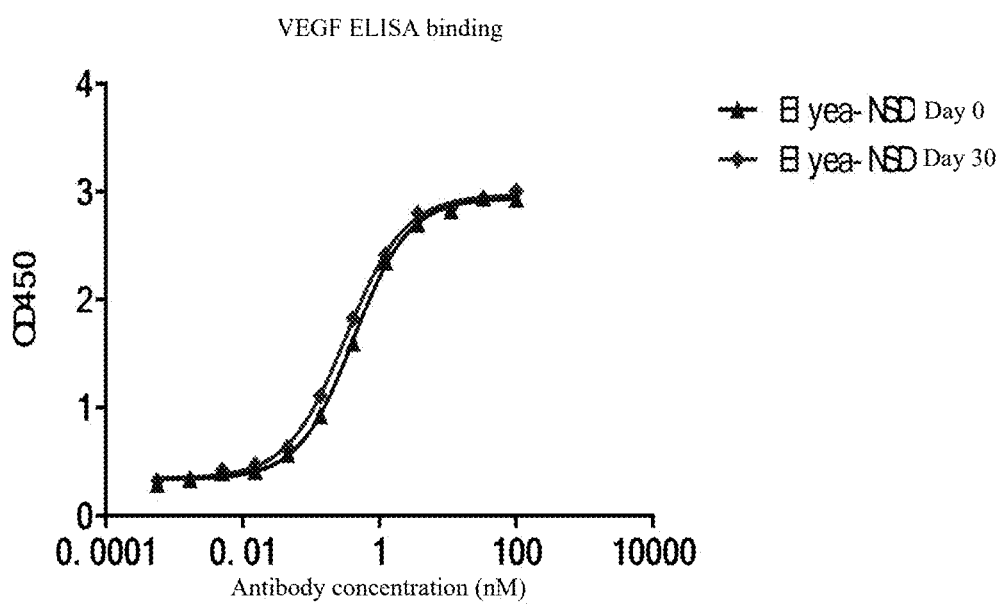
FIG. 5G shows the binding curves of the bispecific antibody stored for different days to VEGF.
Figure 5H:
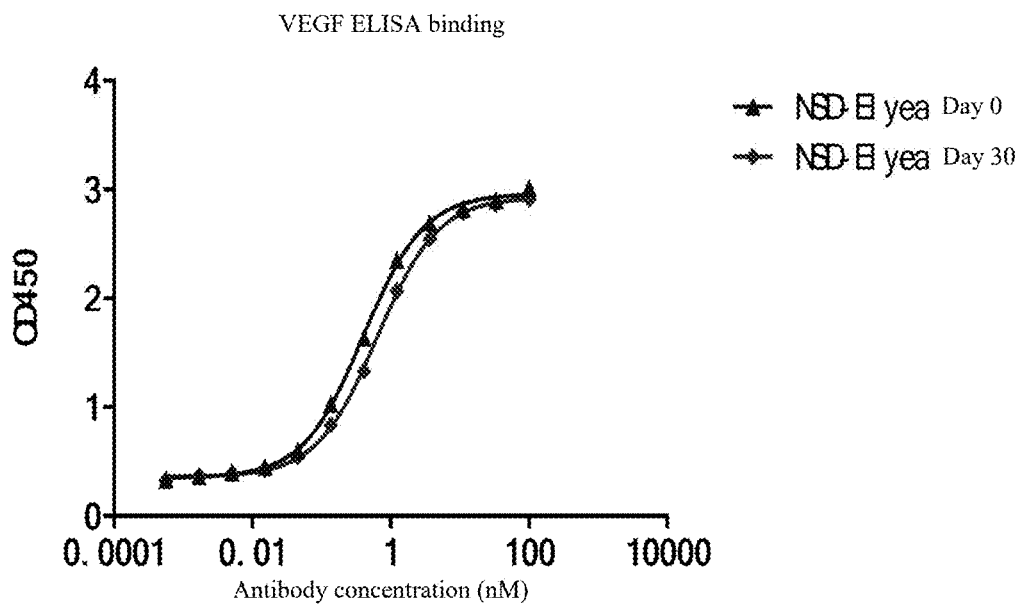
FIG. 5H shows the binding curves of the bispecific antibody stored for different days to VEGF.

The results were shown in FIG. 4A and FIG. 4B, in which Ava-2GS-NSD, Luc-2GS-NSD, Ava-4GS-NSD, Luc-4GS-NSD, NSD-Elyea, Elyea-NSD all showed good biological activity in the MLR experiment, and the activation levels were comparable to or better than that of the control antibody C-Ye-18-5. For example, at some concentrations, the bispecific antibody samples induced higher secretion of IL2 or INF than the control antibody, showing that the bispecific antibody of the present invention could better activate T cells.

Example 6: Accelerated Stability Test 6.1 Purity Determination of Accelerated Stability Test Samples In this experiment, the long-term thermal stability of the bispecific antibody was evaluated by detecting the changes of purity and biological activity of the bispecific antibody after being placed at 40° C. for 30 days. The purity of the target antibody after storage at 40° C. for 0, 14 and 30 days was determined by SEC.

The experimental results were shown in Table 3.

TABLE 3

Monomer ratio of accelerated stability test sample

| Sample name | Day 0 | Day 14 | Day 30 |
|---|---|---|---|
| Ava-2GS-NSD | 98.9% | 98.1% | 97.0% |
| Luc-2GS-NSD | 97.4% | 97.3% | 96.3% |
| NSD-Elyea | 93.0% | 97.1% | 94.1% |
| Elyea-NSD | 99.7% | 100.0% | 98.4% |

The results showed that the purity of bispecific antibodies Ava-2GS-NSD, Luc-2GS-NSD, NSD-Elyea, and Elyea-NSD did not change significantly.

6.2 Activity Determination of Accelerated Stability Test Sample

In this experiment, the FACS method was used to detect the binding of the accelerated stability test samples to CHO-PDL1 cells, and the method was as Example 3. The binding of the accelerated stability test samples to VEGF was detected by the following ELISA method: VEGFA recombinant protein was diluted to 1 μg/ml with ELISA coating solution, added to the ELISA plate, 100 μl/well, and coated overnight at 4° C. The coating solution was discarded, PBST was added, 250 μl/well, to wash 3 times, and blocking was carried out with 5% BSA for 1 hour at room temperature. The purified samples were serially diluted with 1% BSA. The blocking solution was discarded from the ELISA plate, the diluted samples above were added to the blocked ELISA plate, 100 μl/well, and incubated at room temperature for 2 hours. PBST was added, 250 μl/well, to wash 3 times, the goat anti-human Fc-HRP diluted with 1% BSA was added, 100 μl/well, and incubated at room temperature for 1 hour, PBST was added, 250 μl/well, to wash 3 times, ELISA chromogenic solution was added, 100 μl/well, and allowed to stand at room temperature for 3 minutes. ELISA stop solution was added, 50 μl/well, and the absorbance value at 450 nm was read.

The experimental results were shown in FIG. 5A to FIG. 5H, the EC50 values of the bispecific antibody to bind to CHO-PDL1 cells (FIG. 5A to FIG. 5D) and VEGF protein (FIG. 5E to FIG. 5H) did not change significantly. The results showed that the bispecific antibodies of the present invention had good thermal stability.

Example 7: Pharmacokinetic Evaluation in Rats

In this experiment, the pharmacokinetic properties of the anti-PD-L1/VEGF bispecific antibody were tested in rats, in which 6 SD rats (half male and half female, 12/12 hour light/dark adjustment, temperature 24+2° C., humidity 40-70%, free access to water and diet) were purchased from Zhejiang Weitong Lihua Experimental Technology Co., Ltd. On the day of the experiment, Ava-2GS-NSD or Elyea-NSD molecules were injected into the tail vein of the SD rats once at the dose of 10 mg/kg.

Blood collection time points: blood samples were collected from the jugular vein of rats at 3 minutes, 4 hours, 10 hours, 24 hours, 48 hours, 72 hours, 120 hours, 168 hours, 240 hours, 336 hours, 504 hours and 672 hours after administration. The whole blood samples were allowed to stand at 2-8° C. for 30 minutes, then centrifuged at 12,000 rpm for 5 minutes to collect sera. The obtained sera were centrifuged at 2-8° C., 12,000 rpm for 5 minutes, stored at −80° C., and the free Ava-2GS-NSD or Elyea-NSD molecules in the sera were detected by ELISA.

The experimental results were shown in Table 4.

TABLE 4

T½ of bispecific antibodies in SD rats

| Tested drug | Administration method | T½ |
|---|---|---|
| Ava-2GS-NSD | IV | 320.6 hours |
| Elyea-NSD | IV | 38.1 hours |

The results showed that the half-life of Ava-2GS-NSD molecule of the present invention in the SD rats was about 320.6 hours, and the half-life of Elyea-NSD molecule in the SD rats was about 38.1 hours.

Example 8: Tumor Suppressive Activity of Bispecific Antibody

In this experiment, the human colon cancer LOVO cells/NOG mice injected with human PBMC model was used to determine the anti-tumor effect of the bispecific antibody. Sufficient LOVO cells (purchased from Addexbio) were cultured and expanded in vitro, collected after trypsinization, washed with PBS for 3 times, counted, and inoculated into 8-week-old female NOG severe immunodeficiency mice (purchased from Beijing Weitong Lihua Experimental Animal Technology Co., Ltd.) subcutaneously on the right abdomen of mice at the amount of 2×106 cells/mouse. The subcutaneous tumor formation was observed daily, and 6×106 PBMCs were injected into the tail vein of each mouse 8 days after inoculation. 3 days after the injection of PBMCs, the maximum axial width W and maximum axial length L of the subcutaneous tumor in the right abdomen of each animal were measured using caliper, and the body weight of each mouse was weighed using electronic balance. The subcutaneous tumor volume of the right abdomen of each mouse was calculated according to the formula: tumor volume T=½×W×W×L. The mice with too large or too small tumor volume were excluded, and the NOG mice were divided into 4 groups according to the average tumor volume, 6 mice in each group. The grouping was carried out according to the grouping regimen shown in Table 5 below, and corresponding doses of Ava-2GS-NSD were injected.

TABLE 5

Experimental protocol for tumor suppressive activity of anti-PD-L1/VEGF bispecific antibody

| Group | Administrated drug | Dose | Dosing frequency |
|---|---|---|---|
| Group 1 | PBS | — | 2 times per week, 6 times in total |
| Group 2 | Ava-2GS-NSD | 24 mg/kg | 2 times per week, 6 times in total |
| Group 3 | Ava-2GS-NSD | 4.8 mg/kg | 2 times per week, 6 times in total |
| Group 4 | Ava-2GS-NSD | 1 mg/kg | 2 times per week, 6 times in total |

The tumor volume and body weight of the mice were measured twice per week. The body weight and tumor volume of the mice were measured for the last time at the 31st day after tumor cell inoculation, and the mice were euthanized.

Figure 6A:
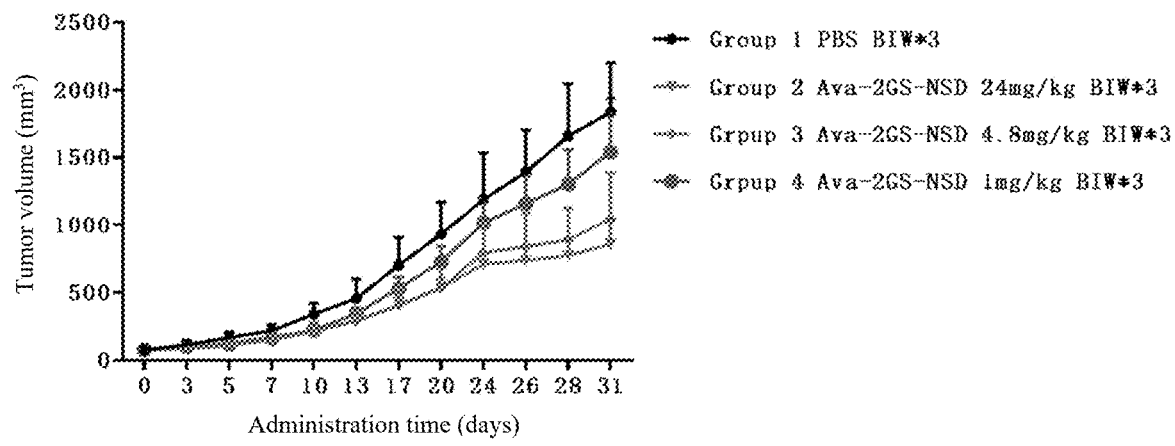
FIG. 6A shows the diagram of the effect of the bispecific antibody on the tumor volume in mice.
Figure 6B:
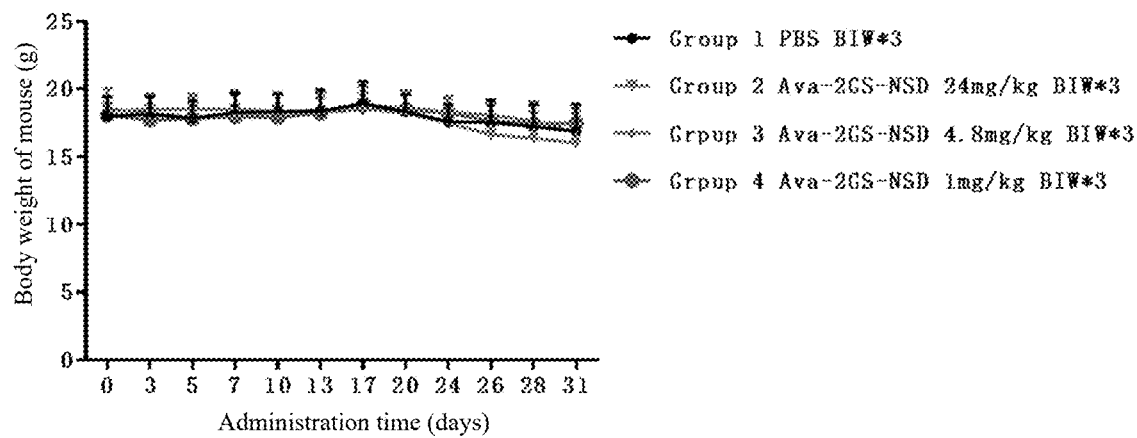
FIG. 6B shows the diagram of the effect of the bispecific antibody on the body weight of mice.

The experimental results were shown in FIG. 6A, FIG. 6B and Table 6.

TABLE 6

Effects of each treatment group on volume and TGI of LOVO tumor inoculated subcutaneously in NOG mice

| Group | Administrated drug | Dose (mg/kg) | Tumor volume (mm³) | | Tumor regression number | Tumor growth inhibition rate TGI (%) |
|---|---|---|---|---|---|---|
| | | | D31 | D0 | | |
| Group 1 | PBS | N/A | 1837.18 | 77.49 | 0 | N/A |
| Group 2 | Ava-2GS-NSD | 24 | 858.44*** | 77.65 | 0 | 55.6% |
| Group 3 | Ava-2GS-NSD | 4.8 | 1047.51** | 77.85 | 0 | 44.9% |
| Group 4 | Ava-2GS-NSD | 1 | 1542.63 | 77.78 | 0 | 16.7% |

Note:
Compared with PBS group,
***represented P < 0.001;
**represented P < 0.01.

The results showed that, compared with the PBS group, Ava-2GS-NSD could inhibit tumor growth in a dose-dependent manner, and the TGI values at 1 mg/kg, 4.8 mg/kg and 24 mg/kg doses were 16.7%, 44.9% and 55.6%, respectively. The tumor volume of the 4.8 mg/kg and 24 mg/kg groups was significantly different from that of the PBS group. The results of average tumor weight, tumor growth inhibition rate and tumor volume substantially showed similar trend (FIG. 6A and Table 6).

The daily observation of the mice in each group showed no abnormality: the body weight of the mice was measured twice per week, and the body weight of the mice in each group did not decrease significantly: at the end of the experiment, the body weight of the mice in each dose group had changed no more than 13% compared to their weight at the beginning of the administration and treatment, and the body weight of the mice in the PBS group decreased by 6%; so it was considered that it was more likely that the body weight of the mice in each group decreased in the later stage of the experiment due to the GvHD caused by the reconstitution of PBMC in the mice (see FIG. 6B). At the end of the experiment, the mice in each group were dissected for the inspection of liver, kidney, lung and other major organs. No obvious lesions were found, indicating that the drugs in each group had no obvious toxicity to the mice under the doses used in this experiment.

The experimental results showed that Ava-2GS-NSD could inhibit the growth of LOVO subcutaneous transplanted tumors in a dose-dependent manner, and the effective dose was 4.8 mg/kg; and no obvious toxicity to mice was observed at the 3 doses (1 mg/kg. 4.8 mg/kg and 24 mg/kg).

All documents mentioned in the present application are incorporated by reference in the present application as if each of them was individually incorporated by reference. In addition, it should be understood that after reading the above teaching content of the present invention, those skilled in the art can make various changes or modifications to the present invention, and these equivalent forms also fall within the scope defined by the appended claims of the present application.

What is claimed is:

1. A bispecific antibody comprising:
a first protein functional region targeting VEGF, and
a second protein functional region targeting PD-L1;
wherein the first protein functional region is an anti-VEGF antibody or an antigen-binding fragment thereof,
wherein the anti-VEGF antibody or antigen-binding fragment thereof comprises a heavy chain variable region (VH) comprising:
HCDR1 with an amino acid sequence as set forth in SEQ ID NO: 21, HCDR2 with an amino acid sequence as set forth in SEQ ID NO: 22, and HCDR3 with an amino acid sequence as set forth in SEQ ID NO: 23; or
HCDR1 with an amino acid sequence as set forth in SEQ ID NO: 27, HCDR2 with an amino acid sequence as set forth in SEQ ID NO: 22, and HCDR3 with an amino acid sequence as set forth in SEQ ID NO: 28; and
wherein the anti-VEGF antibody or antigen-binding fragment thereof comprises a light chain variable region (VL) comprising:
LCDR1 with an amino acid sequence as set forth in SEQ ID NO: 24, LCDR2 with an amino acid sequence as set forth in SEQ ID NO: 25, and LCDR3 with an amino acid sequence as set forth in SEQ ID NO: 26;
wherein the second protein functional region is an anti-PD-L1 single-domain antibody,
wherein the anti-PD-L1 single-domain antibody comprises a heavy chain variable region, and the heavy chain variable region comprises HCDR1 with an amino acid sequence as set forth in SEQ ID NO: 29, HCDR2 with an amino acid sequence as set forth in SEQ ID NO: 30, and HCDR3 with an amino acid sequence as set forth in SEQ ID NO: 31.

2. The bispecific antibody according to claim 1, wherein the anti-VEGF antibody or antigen-binding fragment thereof comprises a heavy chain variable region with an amino acid sequence as set forth in SEQ ID NO: 3, and a light chain variable region with an amino acid sequence as set forth in SEQ ID NO: 9; or the anti-VEGF antibody or antigen-binding fragment thereof comprises a heavy chain variable region with an amino acid sequence as set forth in SEQ ID NO: 13, and a light chain variable region with an amino acid sequence as set forth in SEQ ID NO: 15.

3. The bispecific antibody according to claim 1, wherein the anti-VEGF antibody or antigen-binding fragment thereof comprises a human IgG1 constant region.

4. The bispecific antibody according to claim 3, wherein the anti-VEGF antibody or antigen-binding fragment thereof comprises a heavy chain constant region that is a human IgG1 and comprises a light chain constant region that is a human kappa light chain constant region.

5. The bispecific antibody according to claim 3, wherein the anti-VEGF antibody or antigen-binding fragment thereof comprises a heavy chain constant region that comprises a L234A mutation and a L235A mutation according to EU numbering system.

6. The bispecific antibody according to claim 3, wherein the anti-PD-L1 single-domain antibody is ligated to the C-terminus or N-terminus of the first protein functional region;
and the single domain antibody is ligated directly or through a linking fragment to the first protein functional region.

7. The bispecific antibody according to claim 3, wherein the bispecific antibody comprises polypeptides with structures shown in Formula I and Formula II, A1-L1-CH-L2-B (Formula I)

A2-L3-CL (Formula II)

wherein
A1 represents the heavy chain variable region VH of the anti-VEGF antibody;
A2 represents the light chain variable region VL of the anti-VEGF antibody;
B represents the anti-PD-L1 single domain antibody;
L1, L2 and L3 each independently represent an optional linker which may be independently selected;
CH represents a human IgG heavy chain constant region CH;

CL represents the human kappa light chain constant region CL; and

"-" represents a peptide bond; and wherein the polypeptide represented by Formula I and the polypeptide represented by Formula II form a heterodimer through disulfide bond interaction.

8. The bispecific antibody according to claim 1, wherein the heavy chain variable region of the anti-VEGF antibody or antigen-binding fragment thereof comprises an HCDR1 with the amino acid sequence set forth in SEQ ID NO: 21, HCDR2 with the amino acid sequence set forth in SEQ ID NO: 22, and HCDR3 with the amino acid sequence set forth in SEQ ID NO: 23.

9. The bispecific antibody according to claim 1, wherein the heavy chain variable region of the anti-VEGF antibody or antigen-binding fragment thereof comprises an HCDR1 with the amino acid sequence set forth in SEQ ID NO: 27, HCDR2 with the amino acid sequence set forth in SEQ ID NO: 22, and HCDR3 with the amino acid sequence set forth in SEQ ID NO: 28.

10. The bispecific antibody according to claim 1, wherein the anti-VEGF antibody or antigen-binding fragment thereof comprises a heavy chain variable region with the amino acid sequence set forth in SEQ ID NO: 3 and a light chain variable region with the amino acid sequence set forth in SEQ ID NO: 9.

11. The bispecific antibody according to claim 3, wherein the anti-VEGF antibody or antigen-binding fragment thereof comprises a heavy chain variable region with the amino acid sequence set forth in SEQ ID NO: 13 and a light chain variable region with the amino acid sequence set forth in SEQ ID NO: 15.

12. The bispecific antibody according to claim 3, wherein the anti-PD-L1 single-domain antibody comprises the amino acid sequence set forth in SEQ ID NO: 5.

13. The bispecific antibody according to claim 1, wherein the anti-VEGF antibody or antigen-binding fragment thereof comprises a light chain constant region with the amino acid sequence set forth in SEQ ID NO: 10.

14. The bispecific antibody according to claim 1, wherein the anti-VEGF antibody or antigen-binding fragment thereof comprises a light chain with the amino acid sequence set forth in SEQ ID NO: 8 or SEQ ID NO: 14.

15. The bispecific antibody according to claim 1, wherein the anti-VEGF antibody or antigen-binding fragment thereof comprises a light chain with the amino acid sequence set forth in SEQ ID NO: 8.

16. The bispecific antibody according to claim 1, wherein the anti-VEGF antibody or antigen-binding fragment thereof comprises a heavy chain constant region with the amino acid sequence set forth in SEQ ID NO: 4.

17. The bispecific antibody according to claim 3, wherein the anti-VEGF antibody or antigen-binding fragment thereof comprises a heavy chain variable region with the amino acid sequence set forth in SEQ ID NO: 3 and a light chain variable region with the amino acid sequence set forth in SEQ ID NO: 9; and the anti-PD-L1 single-domain antibody comprises the amino acid sequence set forth in SEQ ID NO: 5.

18. The bispecific antibody according to claim 3, wherein the anti-VEGF antibody or antigen-binding fragment thereof comprises a heavy chain with the amino acid sequence set forth in SEQ ID NO: 1.

19. The bispecific antibody according to claim 7, wherein L2 comprises the amino acid sequence set forth in SEQ ID NO: 6.

20. The bispecific antibody according to claim 7, wherein L2 comprises the amino acid sequence set forth in SEQ ID NO: 7.

21. The bispecific antibody according to claim 1, wherein the anti-VEGF antibody or antigen-binding fragment thereof comprises a heavy chain with the amino acid sequence set forth in SEQ ID NO: 2, SEQ ID NO: 11, or SEQ ID NO: 12.

22. The bispecific antibody according to claim 6, wherein the anti-PD-L1 single-domain antibody is ligated to the C-terminus or N-terminus of a first heavy chain of the first protein functional region.

23. The bispecific antibody according to claim 22, further comprising a second anti-PD-L1 single-domain antibody, wherein the second anti-PD-L1 single-domain antibody is ligated to the C-terminus or N-terminus of a second heavy chain of the first protein functional region.

24. The bispecific antibody according to claim 3, wherein the anti-VEGF antibody or antigen-binding fragment thereof comprises a heavy chain variable region with the amino acid sequence set forth in SEQ ID NO: 3 and a light chain variable region with the amino acid sequence set forth in SEQ ID NO: 9; the anti-PD-L1 single-domain antibody comprises the amino acid sequence set forth in SEQ ID NO: 5; wherein the anti-VEGF antibody or antigen-binding fragment thereof further comprises a human IgG heavy chain constant region and a human kappa light chain constant region.

25. The bispecific antibody according to claim 24, wherein the human IgG heavy chain constant region has a LALA mutation.

26. The bispecific antibody according to claim 24, wherein the human IgG heavy chain constant region comprises the amino acid sequence set forth in SEQ ID NO: 4.

27. The bispecific antibody according to claim 25, wherein the human kappa light chain constant region comprises the amino acid sequence set forth in SEQ ID NO: 10.

28. The bispecific antibody according to claim 24, wherein the bispecific antibody comprises polypeptides with structures shown in Formula I and Formula II, A1-L1-CH-L2-B (Formula I)

A2-L3-CL (Formula II)

wherein

A1 represents the heavy chain variable region VH of the anti-VEGF antibody;

A2 represents the light chain variable region VL of the anti-VEGF antibody;

B represents the anti-PD-L1 single domain antibody;

L1, L2 and L3 each independently represent an optional linker which may be independently selected;

CH represents a human IgG heavy chain constant region CH;

CL represents the human kappa light chain constant region CL; and

"-" represents a peptide bond; and wherein the polypeptide represented by Formula I and the polypeptide represented by Formula II form a heterodimer through disulfide bond interaction.

29. The bispecific antibody according to claim 27, wherein the human IgG heavy chain constant region CH comprises the amino acid sequence set forth in SEQ ID NO: 4.

30. The bispecific antibody according to claim 28, the human kappa light chain constant region CL comprises the amino acid sequence set forth in SEQ ID NO: 10.

31. The bispecific antibody according to claim 29, wherein L2 comprises the amino acid sequence set forth in SEQ ID NO: 6 or SEQ ID NO: 7.

32. A pharmaceutical composition, which comprises the bispecific antibody according to claim 1; and a pharmaceutically acceptable excipient.

33. A pharmaceutical composition, wherein the pharmaceutical composition comprises:
   (i) the bispecific antibody of claim 7; and
   (ii) a pharmaceutically acceptable carrier.

34. A pharmaceutical composition, wherein the pharmaceutical composition comprises:
   (i) the anti-VEGF/PD-L1 bispecific antibody of claim 24; and
   (ii) a pharmaceutically acceptable carrier.

* * * * *

UNITED STATES PATENT AND TRADEMARK OFFICE
CERTIFICATE OF CORRECTION

PATENT NO. : 12,325,759 B2  
APPLICATION NO. : 18/023701  
DATED : June 10, 2025  
INVENTOR(S) : Xiaoniu Miao et al.

Page 1 of 1

It is certified that error appears in the above-identified patent and that said Letters Patent is hereby corrected as shown below:

In the Claims

In Claim 4, Column 76, Line 32, after "claim" delete "3," and insert -- 1, --.  
In Claim 5, Column 76, Line 37, after "claim" delete "3," and insert -- 1, --.  
In Claim 6, Column 76, Line 42, after "claim" delete "3," and insert -- 1, --.  
In Claim 7, Column 76, Line 50, after "claim" delete "3," and insert -- 1, --.  
In Claim 11, Column 77, Line 28, after "claim" delete "3," and insert -- 1, --.  
In Claim 12, Column 77, Line 34, after "claim" delete "3," and insert -- 1, --.  
In Claim 17, Column 77, Line 53, after "claim" delete "3," and insert -- 1, --.  
In Claim 18, Column 77, Line 61, after "claim" delete "3," and insert -- 1, --.  
In Claim 24, Column 78, Line 17, after "claim" delete "3," and insert -- 1, --.

Signed and Sealed this  
Fourteenth Day of October, 2025

John A. Squires  
*Director of the United States Patent and Trademark Office*